(12) United States Patent
Yanagidate

(10) Patent No.: US 10,250,853 B2
(45) Date of Patent: Apr. 2, 2019

(54) WIRELESS ENDOSCOPE SYSTEM, ENDOSCOPE, DISPLAY DEVICE, IMAGE TRANSMISSION METHOD, IMAGE DISPLAY METHOD, AND PROGRAM

(71) Applicant: OLYMPUS CORPORATION, Hachioji-shi, Tokyo (JP)

(72) Inventor: Masaharu Yanagidate, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 113 days.

(21) Appl. No.: 15/290,490

(22) Filed: Oct. 11, 2016

(65) Prior Publication Data

US 2017/0034484 A1    Feb. 2, 2017

Related U.S. Application Data

(63) Continuation of application No. PCT/JP2015/061551, filed on Apr. 15, 2015.

(30) Foreign Application Priority Data

May 22, 2014    (JP) ................................. 2014-106348

(51) Int. Cl.
*H04N 7/18* (2006.01)
*A61B 1/04* (2006.01)
(Continued)

(52) U.S. Cl.
CPC ........... *H04N 7/185* (2013.01); *A61B 1/0002* (2013.01); *A61B 1/00009* (2013.01);
(Continued)

(58) Field of Classification Search
CPC .................................................... H04N 7/185
See application file for complete search history.

(56) References Cited

U.S. PATENT DOCUMENTS 9,621,900 B1 * 4/2017 Ostiguy ............... H04N 19/136
2004/0259065 A1 * 12/2004 Geiger .................... G06T 5/009
434/272
(Continued)

FOREIGN PATENT DOCUMENTS

JP          7-284095          10/1995
JP          10-323326 A       12/1998
(Continued)

OTHER PUBLICATIONS

International Search Report dated Jun. 30, 2015, issued in counterpart International Application No. PCT/JP2015/061551 (1 page).
(Continued)

*Primary Examiner* — Jayanti K Patel
*Assistant Examiner* — Shadan E Haghani
(74) *Attorney, Agent, or Firm* — Westerman, Hattori, Daniels & Adrian, LLP

(57) ABSTRACT

A wireless endoscope system includes: a data storage unit that stores imaging data as storage data at a time at which a still image display signal is switched from a first state indicating an execution of a moving image display to a second state indicating an execution of a still image display; an image quality control unit that controls image quality of a plurality of pieces of still image data such that an image quality of a piece of still image data generated later a becomes higher; a data-selecting unit that selects the moving image data or the plurality of pieces of still image data on the basis of the still image display signal; and a transmission unit that transmits the moving image data or the plurality of pieces of still image data selected by the data-selecting unit in a wireless manner.

9 Claims, 12 Drawing Sheets

(51) Int. Cl.
  *H04N 19/59*   (2014.01)
  *A61B 1/00*    (2006.01)
  *H04N 5/232*   (2006.01)
  *H04N 5/44*    (2011.01)
  *H04N 5/46*    (2006.01)
  *G02B 23/24*   (2006.01)
  *H04N 5/225*   (2006.01)

(52) U.S. Cl.
  CPC ............ *A61B 1/00016* (2013.01); *A61B 1/04* (2013.01); *H04N 5/23232* (2013.01); *H04N 5/23293* (2013.01); *H04N 5/4448* (2013.01); *H04N 5/46* (2013.01); *H04N 19/59* (2014.11); *G02B 23/2484* (2013.01); *H04N 2005/2255* (2013.01)

(56) References Cited

U.S. PATENT DOCUMENTS

| | | | |
|---|---|---|---|
| 2007/0167754 A1* | 7/2007 | Okuno | A61B 1/0005 600/437 |
| 2012/0134410 A1 | 5/2012 | Kawasaki et al. | |
| 2015/0208900 A1* | 7/2015 | Vidas | A61B 1/00009 348/74 |

FOREIGN PATENT DOCUMENTS

| | | |
|---|---|---|
| JP | 3227834 B | 11/2001 |
| JP | 2009-100935 A | 5/2009 |
| JP | 2010-251902 A | 11/2010 |
| JP | 2010-288186 A | 12/2010 |
| JP | 2012-120578 A | 6/2012 |
| JP | 2013-128723 A | 7/2013 |

OTHER PUBLICATIONS

Yasuda, "International Standard of Multimedia Encoding", Maruzen Co., Ltd., pp. 24-26, 1991 (w/partial translation).

Notice of Reason for Rejection dated Mar. 13, 2018, issued in Japanese application No. 2014-106348, with partial English translation. (4 pages).

Notice of Allowance dated Oct. 2, 2018, issued in counterpart Japanese Application No. 2014-106348, with English translation (6 pages).

\* cited by examiner

FIG. 2
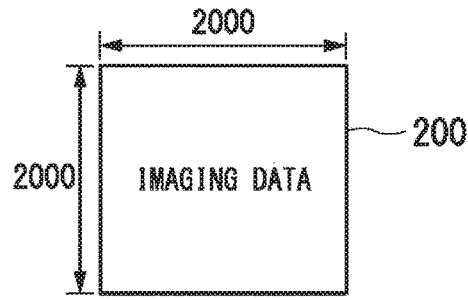
FIG. 3
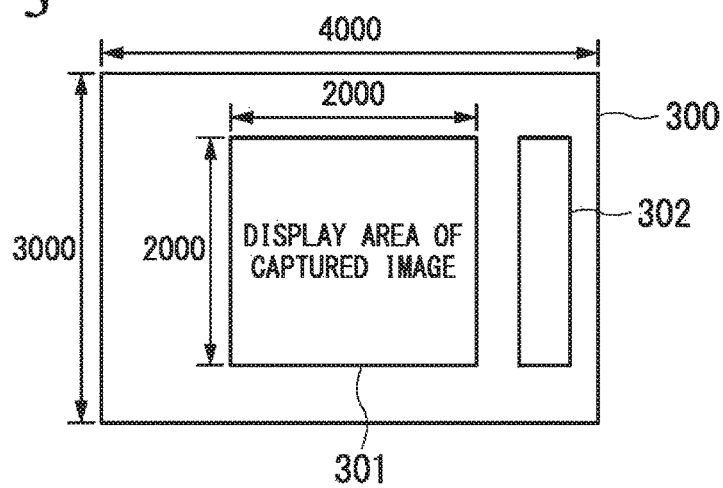
FIG. 4
| FORMAT | PIXEL CONFIGURATION | COMPRESSION RATE | TRANSMISSION TIME |
|---|---|---|---|
| MOVING IMAGE | 1000 × 1000 | 1/20 | 0.033s (30f/s) |
| FIRST STILL IMAGE | 2000 × 2000 | 1/20 | 0.133s |
| SECOND STILL IMAGE | 2000 × 2000 | 1/4 | 0.667s |
| THIRD STILL IMAGE | 2000 × 2000 | 1/1 | 2.667s |

WIRELESS ENDOSCOPE SYSTEM, ENDOSCOPE, DISPLAY DEVICE, IMAGE TRANSMISSION METHOD, IMAGE DISPLAY METHOD, AND PROGRAM

This application is a continuation application based on a PCT International Application No. PCT/JP2015/061551, filed on Apr. 15, 2015, whose priority is claimed on Japanese Patent Application No. 2014-106348, filed May 22, 2014. Both of the content of the PCT International Application and the Japanese Application are incorporated herein by reference.

BACKGROUND OF THE INVENTION

Field of the Invention
Description of Related Art
In an endoscope system, a still image for detailed observation may be stored during observation of a moving image. The storage of a still image is performed in response to a freeze instruction from an operator. The stored still image is used for a diagnosis of a lesion. In order to facilitate the diagnosis easily, the still image is required to be a high-definition image. In order to improve workability of an operator, a display delay is required to be small.

In a wireless endoscope that transmits a still image in a wireless manner, a transmission channel band is limited. Accordingly, it is difficult to transmit a high-definition image while reducing a display delay. The wireless endoscope is driven with a battery in order to improve portability. Accordingly, a reduction in circuit scale and a simplification of processes are required for power saving.

In order to solve these problems, a wireless endoscope may separately transmit a low-resolution moving image for normal observation and a high-resolution still image for detailed observation. Patent Literature 1 discloses the following image-processing device. The image-processing device selects encoding to be performed on image data among encoding for a moving image and encoding for a still image on the basis of an instruction from an instruction unit. The encoded image data is transmitted to an external device. Patent Literature 1 also discloses an example in which transmission of a moving image can be interrupted and a high-definition still image can be instead transmitted in response to an instruction from the instruction unit during transmission of a low-quality moving image.

Aside from the above-mentioned related art, a so-called progressive encoding method which is a part of the Joint Photographic Experts Group (JPEG) standard is disclosed. In this method, a still image of a frame is encoded (corresponding to compression) and the encoded still image of the frame is divided for each frequency component. The frequency components are sequentially transmitted from a low frequency component to a high frequency component. Accordingly, the image quality of a still image to be displayed gradually varies from low image quality to high image quality. Details of the progressive encoding are disclosed in Hiroshi YASUDA, "International Standard of Multimedia Encoding," Maruzen Co., Ltd., July, 1991, p. 24-26.

SUMMARY OF THE INVENTION

According to a first aspect of the present invention, a wireless endoscope system is provided, including: an imaging unit that captures an image and generates imaging data; a freeze-instructing unit that generates a still image display signal relevant to an execution of a still image display; a data storage unit that stores the imaging data as storage data at a time at which the still image display signal is switched from a first state indicating an execution of a moving image display to a second state indicating an execution of the still image display; a moving image-compressing unit that performs a moving image-compressing process on the imaging data and generates moving image data; a still image-compressing unit that performs a still image-compressing process on the storage data and generates a plurality of pieces of still image data; an image quality control unit that controls image quality of the plurality of pieces of still image data such that image quality of a piece of still image data generated later among the plurality of pieces of still image data becomes higher; a data-selecting unit that selects the moving image data when the still image display signal is in the first state and sequentially selects the plurality of pieces of still image data in an order in which the plurality of pieces of still image data are generated when the still image display signal is in the second state; a transmission unit that transmits the moving image data or the plurality of pieces of still image data selected by the data-selecting unit in a wireless manner; a reception unit that receives the moving image data or the plurality of pieces of still image data transmitted from the transmission unit in a wireless manner; an image-decompressing unit that performs a decompressing process on the moving image data or the plurality of pieces of still image data received by the reception unit and generates display data, the image-decompressing unit generating a plurality of pieces of display data in the order in which the plurality of pieces of still image data are generated in the decompressing process on the plurality of pieces of still image data; an image display unit that performs a display process based on the display data; a target image-designating unit that designates the display data as target image data when the image quality of the piece of still image data is equal to or higher than a predetermined image quality; and an image storage unit that stores the display data designated as the target image data According to a second aspect of the present invention, the wireless endoscope system according to the first aspect wherein the target image-designating unit may designate the display data as target image data when image quality of a piece of still image data corresponding to the display data generated by the image-decompressing unit at a time immediately before the still image display signal is switched from the second state to the first state is equal to or higher than a predetermined image quality.

According to a third aspect of the present invention, the wireless endoscope system according to the first aspect may further include a control unit that controls a generation of the plurality of pieces of still image data on the basis of execution information indicating whether generation of each of the plurality of pieces of still image data should be executed.

According to a fourth aspect of the present invention, the wireless endoscope system according to the first aspect may further include a high image quality-requesting unit that generates a high definition request signal relevant to a request for a piece of still image data with a predetermined highest image quality. The image quality control unit may set the image quality of the piece of still image data to the highest image quality when the still image display signal is in the second state and the high definition request signal is in a third state indicating a request for still image data with the highest image quality before a final piece of still image data among the plurality of pieces of still image data is generated. The image quality control unit may gradually change the image quality of the plurality of pieces of still image data such that the image quality of the piece of still image data generated later becomes higher and image quality of a piece of still image data generated finally is the highest image quality when the still image display signal is in the second state and the high definition request signal is in a fourth state other than the third state before the final piece of still image data among the plurality of pieces of still image data is generated.

According to a fifth aspect of the present invention, an endoscope is provided, including: an imaging unit that captures an image and generates imaging data;

a freeze-instructing unit that generates a still image display signal relevant to an execution of a still image display; a data storage unit that stores the imaging data as storage data at a time at which the still image display signal is switched from a first state indicating an execution of a moving image display to a second state indicating an execution of the still image display; a moving image-compressing unit that performs a moving image-compressing process on the imaging data and generates moving image data; a still image-compressing unit that performs a still image-compressing process on the storage data and generates a plurality of pieces of still image data; an image quality control unit that controls image quality of the plurality of pieces of still image data such that image quality of a piece of still image data generated later among the plurality of pieces of still image data becomes higher; a data-selecting unit that selects the moving image data when the still image display signal is in the first state and sequentially selects the plurality of pieces of still image data in an order in which the plurality of pieces of still image data are generated when the still image display signal is in the second state; and a transmission unit that transmits the moving image data or the plurality of pieces of still image data selected by the data-selecting unit in a wireless manner.

According to a sixth aspect of the present invention, a display device is provided, including: a reception unit that receives moving image data or a plurality of pieces of still image data transmitted from an endoscope in a wireless manner; an image-decompressing unit that performs a decompressing process on the moving image data or the plurality of pieces of still image data received by the reception unit and generates display data, the image-decompressing unit generating a plurality of pieces of display data in an order in which the plurality of pieces of still image data are generated in the decompressing process on the plurality of pieces of still image data; and an image display unit that performs a display process based on the display data, wherein the endoscope includes an imaging unit that captures an image and generates imaging data, a freeze-instructing unit that generates a still image display signal relevant to an execution of a still image display, a data storage unit that stores the imaging data as storage data at a time at which the still image display signal is switched from a first state indicating an execution of a moving image display to a second state indicating an execution of the still image display, a moving image-compressing unit that performs a moving image-compressing process on the imaging data and generates the moving image data, a still image-compressing unit that performs a still image-compressing process on the storage data and generates the plurality of pieces of still image data, an image quality control unit that controls image quality of the plurality of pieces of still image data such that image quality of a piece of still image data generated later among the plurality of pieces of still image data becomes higher, a data-selecting unit that selects the moving image data when the still image display signal is in the first state and sequentially selects the plurality of pieces of still image data in the order in which the plurality of pieces of still image data are generated when the still image display signal is in the second state, and a transmission unit that transmits the moving image data or the plurality of pieces of still image data selected by the data-selecting unit in a wireless manner.

According to a seventh aspect of the present invention, an image transmission method is provided, including: a step of generating a still image display signal relevant to an execution of a still image display by a freeze-instructing unit; a step of storing imaging data which is generated by an imaging unit capturing an image as storage data at a time at which the still image display signal is switched from a first state indicating an execution of a moving image display to a second state indicating an execution of a still image display; a step of performing a moving image-compressing process on the imaging data to generate moving image data by a moving image-compressing unit; a step of performing a still image-compressing process on the storage data by a still image-compressing unit to generate a plurality of pieces of still image data such that image quality of a piece of still image data generated later among the plurality of pieces of still image data becomes higher; a step of transmitting the moving image data in a wireless manner by a transmission unit when the still image display signal is in the first state; and a step of transmitting the plurality of pieces of still image data in a wireless manner in an order in which the plurality of pieces of still image data are generated by the transmission unit when the still image display signal is in the second state.

According to an eighth aspect of the present invention, an image display method is provided, including: a step of receiving moving image data or a plurality of pieces of still image data transmitted from an endoscope in a wireless manner by a reception unit; a step of performing a decompressing process on the moving image data or the plurality of pieces of still image data received by the reception unit and to generate display data, and generating a plurality of pieces of display data in an order in which the plurality of pieces of still image data are generated in the decompressing process on the plurality of pieces of still image data by an image-decompressing unit; and a step of performing a display process based on the display data by an image display unit, wherein the endoscope includes an imaging unit that captures an image and generates imaging data, a freeze-instructing unit that generates a still image display signal relevant to an execution of a still image display, a data storage unit that stores the imaging data as storage data at a time at which the still image display signal is switched from a first state indicating an execution of a moving image display to a second state indicating an execution of the still image display, a moving image-compressing unit that performs a moving image-compressing process on the imaging data and generates the moving image data, a still image-compressing unit that performs a still image-compressing process on the storage data and generates the plurality of pieces of still image data, an image quality control unit that controls image quality of the plurality of pieces of still image data such that image quality of a piece of still image data generated later among the plurality of pieces of still image data becomes higher, a data-selecting unit that selects the moving image data when the still image display signal is in the first state and sequentially selects the plurality of pieces of still image data in the order in which the plurality of pieces of still image data are generated when the still image display signal is in the second state, and a transmission unit that transmits the moving image data or the plurality of pieces of still image data selected by the data-selecting unit in a wireless manner.

According to a ninth aspect of the present invention, a program is provided causing a computer to perform: a step of detecting a still image display signal relevant to an execution of a still image display which is generated by a freeze-instructing unit; a step of causing a data storage unit to store imaging data which is generated by an imaging unit capturing an image as storage data at a time at which the still image display signal is switched from a first state indicating an execution of a moving image display to a second state indicating an execution of the still image display; a step of causing a moving image-compressing unit to perform a process of performing a moving image-compressing process on the imaging data and generating moving image data; a step of causing a still image-compressing unit to perform a process of performing a still image-compressing process on the storage data and generating a plurality of pieces of still image data such that image quality of a piece of still image data generated later among the plurality of pieces of still image data becomes higher; a step of causing a transmission unit to transmit the moving image data in a wireless manner when the still image display signal is in the first state; and a step of causing the transmission unit to transmit the plurality of pieces of still image data in a wireless manner in an order in which the plurality of pieces of still image data are generated when the still image display signal is in the second state.

According to a tenth aspect of the present invention, a program is provided causing a computer to perform: a step of causing a reception unit to receive moving image data or a plurality of pieces of still image data transmitted from an endoscope in a wireless manner; a step of causing an image-decompressing unit to perform a decompressing process on the moving image data or the plurality of pieces of still image data received by the reception unit and to generate display data, and causing the image-decompressing unit to generate a plurality of pieces of display data in an order in which the plurality of pieces of still image data are generated in the decompressing process on the plurality of pieces of still image data; and a step of causing an image display unit to perform a display process based on the display data, wherein the endoscope includes an imaging unit that captures an image and generates imaging data, a freeze-instructing unit that generates a still image display signal relevant to an execution of a still image display, a data storage unit that stores the imaging data as storage data at a time at which the still image display signal is switched from a first state indicating an execution of a moving image display to a second state indicating an execution of the still image display, a moving image-compressing unit that performs a moving image-compressing process on the imaging data and generates the moving image data, a still image-compressing unit that performs a still image-compressing process on the storage data and generates the plurality of pieces of still image data, an image quality control unit that controls image quality of the plurality of pieces of still image data such that image quality of a piece of still image data generated later among the plurality of pieces of still image data becomes higher, a data-selecting unit that selects the moving image data when the still image display signal is in the first state and sequentially selects the plurality of pieces of still image data in the order in which the plurality of pieces of still image data are generated when the still image display signal is in the second state, and a transmission unit that transmits the moving image data or the plurality of pieces of still image data selected by the data-selecting unit in a wireless manner.

BRIEF DESCRIPTION OF THE DRAWINGS

FIG. 2 is a reference diagram illustrating an example of a size of imaging data in the first embodiment of the present invention.

FIG. 3 is a reference diagram illustrating an example of a size of a display screen and a configuration of the display screen in the first embodiment of the present invention.

FIG. 4 is a reference diagram illustrating an example of image data formats, pixel configurations of moving image data and still image data, compression rates, and transmission times per frame.

DETAILED DESCRIPTION OF THE INVENTION

Hereinafter, embodiments of the present invention will be described with reference to the accompanying drawings.

(First Embodiment)

First, a first embodiment of the present invention will be described below. In this embodiment, an example of a wireless endoscope system including an endoscope that transmits a captured image as a moving image or a still image to a display device in a wireless manner and a display device that displays the received moving image or the received still image will be described.

A wireless endoscope system according to this embodiment normally displays a moving image, and displays a still image when an operator issues a freeze instruction. In the display of a still image in this embodiment, an amount of code is reduced and a low-quality image is quickly displayed immediately after the freeze instruction is issued. Thereafter, a high-quality image is gradually displayed. In this display method, the operator can observe a still image displayed immediately after the freeze instruction is issued. When issuance of the freeze instruction continues, the image quality of the displayed still image is gradually changed to high image quality.

Figure 1:
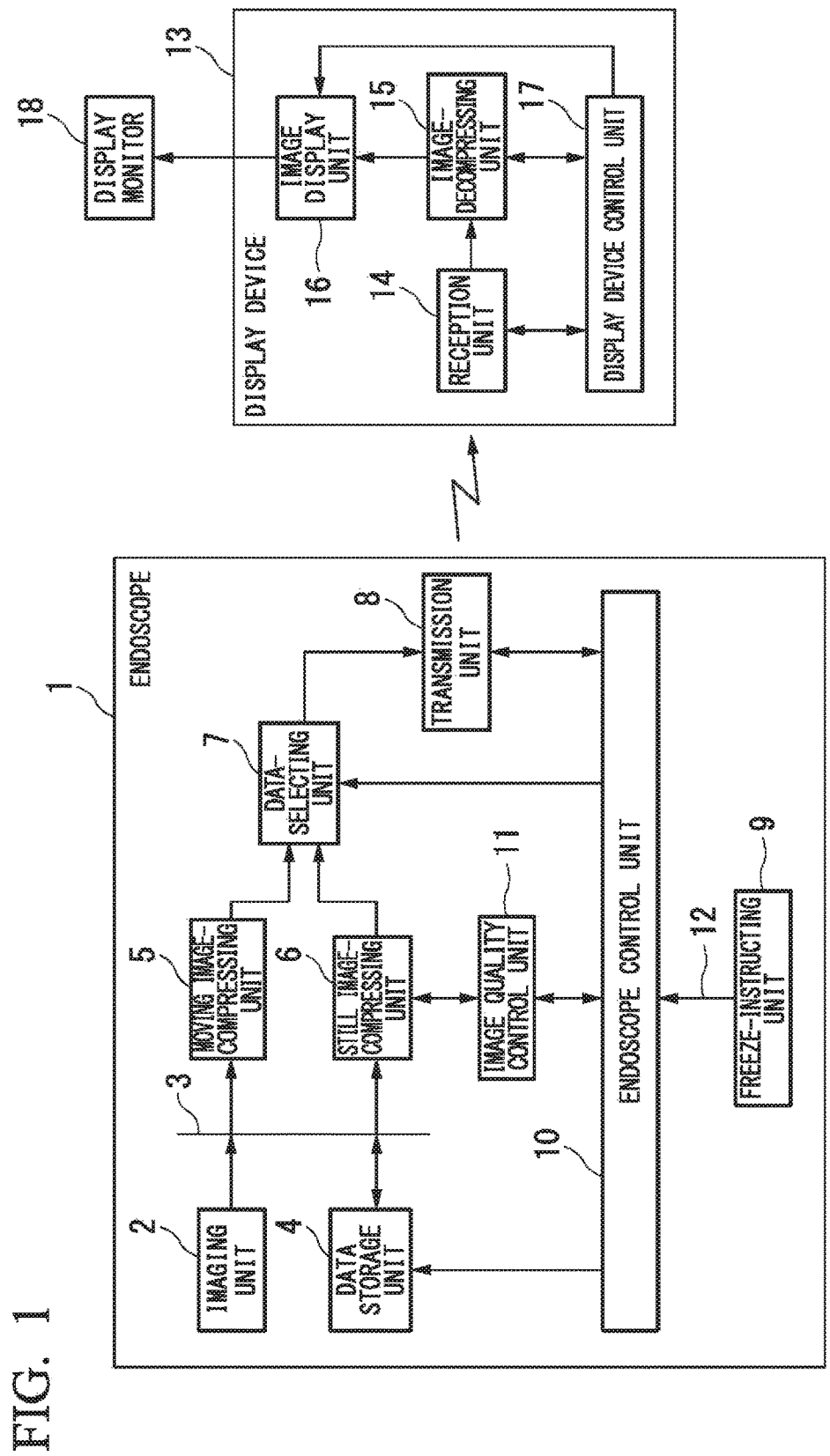
FIG. 1 is a block diagram illustrating an example of a configuration of a wireless endoscope system according to a first embodiment of the present invention.

A configuration and an operation of the wireless endoscope system will be described below with reference to FIGS. 1 to 4. FIG. 1 illustrates an example of the configuration of the wireless endoscope system according to this embodiment. FIG. 2 illustrates an example of a size of imaging data generated by an imaging operation which is performed by an endoscope 1 illustrated in FIG. 1. FIG. 3 illustrates an example of a configuration of a size of a display screen displayed by a display operation which is performed by a display device 13 illustrated in FIG. 1 and a configuration of the display screen. FIG. 4 illustrates an example of transmission times of data per frame of a moving image and a still image.

As illustrated in FIG. 1, the wireless endoscope system according to this embodiment includes the endoscope 1, the display device 13, and a display monitor 18. The endoscope 1 and the display device 13 are connected to each other in a wireless communication manner.

As illustrated in FIG. 1, the endoscope 1 includes an imaging unit 2, a data bus 3, a data storage unit 4, a moving image-compressing unit 5, a still image-compressing unit 6, a data-selecting unit 7, a transmission unit 8, a freeze-instructing unit 9, an endoscope control unit 10, and an image quality control unit 11. The imaging unit 2 is inserted into a living body (a human body), captures an image, and generates imaging data. The imaging data is image data of a subject. The imaging unit 2 outputs the generated imaging data to the data bus 3. The imaging data output from the imaging unit 2 is supplied to the data storage unit 4 and the moving image-compressing unit 5 via the data bus 3.

The data storage unit 4 stores the imaging data output from the imaging unit 2 as storage data. The data storage unit 4 outputs the stored storage data to the data bus 3 in response to an instruction from the endoscope control unit 10. The storage data output from the data storage unit 4 is supplied to the still image-compressing unit 6 via the data bus 3.

The moving image-compressing unit 5 performs a moving image-compressing process on the imaging data and generates moving image data. The moving image-compressing unit 5 outputs the generated moving image data to the data-selecting unit 7. The still image-compressing unit 6 performs a still image-compressing process on the storage data output from the data storage unit 4 and generates a plurality of pieces of still image data. The still image-compressing unit 6 outputs the generated plurality of pieces of still image data to the data-selecting unit 7. The image quality control unit 11 controls the image quality of the plurality of pieces of still image data in response to an instruction from the endoscope control unit 10.

The data-selecting unit 7 selects one of the moving image data output from the moving image-compressing unit 5 and the plurality of pieces of still image data output from the still image-compressing unit 6 on the basis of an instruction from the endoscope control unit 10. The data-selecting unit 7 outputs the selected data to the transmission unit 8. The transmission unit 8 transmits the moving image data or the plurality of pieces of still image data selected by the data-selecting unit 7 to the display device 13 in a wireless manner.

The freeze-instructing unit 9 detects a freeze instruction from an operator of the endoscope 1. In an example of this embodiment, the freeze-instructing unit 9 includes a button and detects the freeze instruction based on a push of the button. The freeze-instructing unit 9 generates a still image display signal 12 relevant to an execution of still image display on the basis of the detection result of the freeze instruction. When the button is not pushed, the still image display signal 12 is in an invalid state (a first state), that is, an OFF state, indicating the execution of a moving image display. When the button is pressed and continues to be pressed, the still image display signal 12 is in a valid state (a second state), that is, an ON state, indicating the execution of a still image display.

The endoscope control unit 10 controls the constituent units of the endoscope 1. Specifically, the endoscope control unit 10 controls the constituent units and performs a freezing process depending on the state of the still image display signal 12. The endoscope control unit 10 may have at least one function of the moving image-compressing unit 5, the still image-compressing unit 6, and the data-selecting unit 7.

The endoscope control unit 10 stores a program for controlling an operation of the endoscope control unit 10 or necessary data. A function of the endoscope control unit 10 can be realized as a software function, for example, by causing a computer of the endoscope 1 to read and execute a program including commands for defining the operation of the endoscope control unit 10. The program may be provided by a "computer-readable recording medium" such as a flash memory. The above-mentioned program may be input to the endoscope 1 by transmitting the program from a computer storing the program in a storage device or the like to the endoscope 1 via a transmission medium or carrier waves in the transmission medium. Here, the "transmission medium" for transmitting the program is a medium having a function of transmitting information like a network (a communication network) such as the Internet or a communication circuit (a communication line) such as a telephone line. The above-mentioned program may realize a part of the above-mentioned functions. The above-mentioned program may be a so-called differential file (a differential program) which can realize the above-mentioned functions in combination with a program which is already recorded in the computer.

When the still image display signal 12 is in the invalid state (the OFF state), a moving image-compressing process and a moving image data-transmitting process for displaying a moving image are performed. The moving image-compressing unit 5 performs the moving image-compressing process. That is, the moving image-compressing unit 5 receives imaging data from the imaging unit 2 and performs the moving image-compressing process on the received imaging data. The data-selecting unit 7 selects the moving image data from the moving image-compressing unit 5. The transmission unit 8 performs the moving image data-transmitting process. That is, the transmission unit 8 receives the moving image data via the data-selecting unit 7 and transmits the received moving image data to the display device 13 in a wireless manner.

When the still image display signal 12 is in the valid state (the ON state), a still image-compressing process and a still image data-transmitting process for displaying a still image are performed. The data storage unit 4 stores imaging data from the imaging unit 2 as storage data at a time at which the still image display signal 12 is switched from the invalid state (the OFF state) indicating an execution of a moving image display to the valid state (the ON state) indicating an execution of a still image display. The still image-compressing unit 6 performs the still image-compressing process. That is, the still image-compressing unit 6 reads the imaging data from the data storage unit 4 and performs the still image-compressing process on the read imaging data.

The still image-compressing unit 6 changes a still image compression parameter and performs the still image-compressing process a plurality of times. The image quality control unit 11 controls the image quality of the plurality of pieces of still image data by setting the still image compression parameter in the still image-compressing unit 6 such that the image quality of a piece of still image data generated later becomes higher. Details of a process of setting the still image compression parameter will be described later. Any one of the plurality of pieces of still image data output from the still image-compressing unit 6 may be data with a compression rate of 1, that is, uncompressed data. That is, the still image-compressing unit 6 may output uncompressed data as still image data.

The data-selecting unit 7 selects the plurality of pieces of still image data generated by the still image-compressing unit 6 in the order in which the plurality of pieces of still image data are generated. The transmission unit 8 performs a process of transmitting the plurality of pieces of still image data. That is, the transmission unit 8 sequentially receives the pieces of still image data via the data-selecting unit 7 and sequentially transmits the received pieces of still image data to the display device 13 in a wireless manner.

The transmission unit 8 transmits management data including a moving image compression parameter or the still image compression parameter and a parameter indicating which of the moving image data and the still image data the image data is (a parameter indicating a type of image data). The management data is transmitted at times immediately before a transmission of a first frame of the moving image data is started and immediately before a transmission of each frame of the still image data is started.

Instead of the moving image compression parameter or the still image compression parameter, information which uniquely corresponds to the parameter and which is other than the parameter may be included in the management data. For example, information for identifying the moving image compression parameter or the still image compression parameter may be included in the management data. Alternatively, information for identifying a moving image format or a still image format may be included in the management data. Instead of the moving image compression parameter or the still image compression parameter, a moving image decompression parameter or a still image decompression parameter corresponding to the parameter may be included in the management data. Alternatively, information for identifying the moving image decompression parameter or the still image decompression parameter may be included in the management data.

Notification of a display end (display switching) of a moving image or a still image is performed using management data other than the above-mentioned management data. The management data for notifying the display end (the display switching) of a moving image or a still image includes data indicating an ending mode (a moving image display mode or a still image display mode). After a state of the still image display signal 12 is changed, the transmission unit 8 transmits the management data to the display device 13 in a wireless manner at a time other than the time at which the moving image data or the still image data is transmitted.

Various formats and transmission times of the image data and the management data have been studied. These are known and thus further description thereof will not be made.

As illustrated in FIG. 1, the display device 13 includes a reception unit 14, an image-decompressing unit 15, an image display unit 16, and a display device control unit 17. The reception unit 14 receives moving image data or a plurality of pieces of still image data which are transmitted from the transmission unit 8 of the endoscope 1 in a wireless manner. The reception unit 14 outputs the received moving image data or the received plurality of pieces of still image data to the image-decompressing unit 15. The image-decompressing unit 15 performs a decompressing process on the received moving image data or the plurality of pieces of still image data and generates display data. The image-decompressing unit 15 generates a plurality of pieces of display data in the order in which the plurality of pieces of still image data are generated in the decompressing process on the plurality of pieces of still image data. The image-decompressing unit 15 outputs the generated display data to the image display unit 16.

The image display unit 16 performs a displaying process using the display data. Specifically, the image display unit 16 converts the display data into data in a format in which an image can be displayed on the display monitor 18. The image display unit 16 outputs the display data having a format converted to the display monitor 18. The display monitor 18 displays a moving image or a still image on the basis of the display data.

The display device control unit 17 controls the constituent units of the display device 13. Specifically, the display device control unit 17 detects the moving image compression parameter or the still image compression parameter and the parameter indicating a type of image data (a moving image or a still image) from the management data received by the reception unit 14. The display device control unit 17 performs setting of the image-decompressing unit 15, setting of the image display unit 16, and setting of the image quality of the still image data on the basis of the detected parameters. The display device control unit 17 may have at least one function of the image-decompressing unit 15 and the image display unit 16.

The display device control unit 17 stores a program for controlling an operation of the display device control unit 17 or necessary data. The function of the display device control unit 17 can be realized as a software function, for example, by causing a computer of the display device 13 to read and execute a program including commands for defining the operation of the display device control unit 17. A method of loading the program may be the same as a method of loading the program for controlling the operation of the endoscope control unit 10 of the endoscope 1.

Image formats in this embodiment will be described below with reference to FIGS. 2 to 4. FIG. 2 illustrates an example of a size of imaging data 200 which is generated by the imaging unit 2. As illustrated in FIG. 2, the imaging data 200 includes pixel data in a square area with a length of 2000 pixels and a width of 2000 pixels. Since the length and the width of an imaging range are changed by rotation when operating the endoscope 1, the area constituting the imaging data has a square shape.

FIG. 3 illustrates an example of a display format of the display monitor 18. In this example, the number of pixels in a length of a display screen 300 of the display monitor 18 is 3000 and the number of pixels in a width of the display screen 300 is 4000. A display area 301 in which an image captured by the endoscope 1 is displayed is set at the center of the display screen 300. An attribute data display area 302 in which the parameter indicating a type of image data (a moving image or a still image) and a parameter indicating image quality of a still image is set in a peripheral portion of the display screen 300.

FIG. 4 illustrates an example of image data formats and pixel configurations, compression rates, and transmission times per frame of moving image data and still image data. The moving image data includes data of pixels in a square area with a length of 1000 pixels and a width of 1000 pixels. Due to the transmission time, the numbers of pixels in the length and the width of the moving image data are numbers of pixels which are obtained by dividing the numbers of pixels in each of the length and the width of the imaging data 200 illustrated in FIG. 2 into halves. The compression rate of the moving image data is set to 1/20. A transmission time per frame to achieve a frame rate (30 f/s) at which 30 frames of moving image data are transmitted per second is 0.033 seconds.

As illustrated in FIG. 4, a format of the still image data is any one of the following three types of still image formats. The pixel configuration of the still image data is the same as the pixel configuration of the imaging data 200 illustrated in FIG. 2. That is, the still image data includes pixel data in the square area with a length of 2000 pixels and a width of 2000 pixels.

In a first still image format, the compression rate is the same as the compression rate of the moving image data, that is, 1/20. In a second still image format, the compression rate is 1/4. In a third still image format, the compression rate is 1. That is, the third still image format corresponds to uncompressed data which is not subject to still image compression. When an amount of data per frame of the moving image data is "1," an amount of data per frame of the still image data in the first still image format is "4." Similarly, an amount of data per frame of the still image data in the second still image format is "20." Similarly, an amount of data per frame of the still image data in the third still image format is "80."

The transmission time per frame illustrated in FIG. 4 is a transmission time when there is no margin in a communication channel and data is transmitted at an upper-limit transmission rate. The transmission time per frame of the moving image data is 0.033 seconds. A transmission time per frame of the still image data in the first still image format is 0.133 seconds. A transmission time per frame of the still image data in the second still image format is 0.667 seconds. A transmission time per frame of the still image data in the third still image format is 2.667 seconds.

When a freeze instruction is issued, a still image display screen including a still image in the first still image format is displayed on the display monitor 18 after about 0.133 seconds passes from a freeze instruction timing. After about 0.8 (0.133+0.667) seconds pass, the still image display screen including the still image in the second still format is displayed on the display monitor 18. After about 3.467 (0.133+0.667+2.667) seconds pass, the still image display screen including the still image in the third still format is displayed on the display monitor 18. These times are calculated on the assumption that the time required for a process other than the transmission process is 0.

The image quality control unit 11 stores the moving image compression parameter and the still image compression parameter corresponding to each format illustrated in FIG. 4. The endoscope control unit 10 notifies the image quality control unit 11 of the formats. The image quality control unit 11 sets the moving image compression parameter or the still image compression parameter corresponding to the notified formats in the moving image-compressing unit 5 or the still image-compressing unit 6.

When a freeze instruction is issued, the endoscope control unit 10 sequentially notifies the image quality control unit 11 of the first to third still image formats. The image quality control unit 11 sequentially selects the still image compression parameter corresponding to the still image formats notified from the endoscope control unit 10 and sets the selected parameter in the still image-compressing unit 6.

Specifically, the image quality control unit 11 sequentially selects the still image compression parameters corresponding to the formats so as to switch the formats in the order of the first still image format, the second still image format, and the third still image format, and sets the selected parameter in the still image-compressing unit 6. That is, the image quality control unit 11 controls the still image compression parameter set in the still image-compressing unit 6 such that the image quality of still image data generated later becomes higher. Accordingly, the image quality control unit 11 can control the image quality of the plurality of pieces of still image data.

As described above, in the example of this embodiment, three types of still image data are used. However, two types of still image data may be used or four or more types of still image data may be used.

In this embodiment, when an execution of a still image display is instructed, first still image data with low image quality in the first still image format is transmitted from the endoscope 1 and a still image based on the first still image data is displayed. Accordingly, it is possible to reduce an initial display delay of a still image.

As described above, in the progressive encoding, an encoded still image of one frame is divided by frequency components and the frequency components are sequentially transmitted. In this embodiment, the encoded still image data of one frame is not divided, but a plurality of pieces of still image data are generated by the still image compression on the imaging data (the storage data). Accordingly, it is possible to more simply perform the still image compression in comparison to progress encoding. Since necessary hardware resources are reduced, it is possible to decrease the size of the endoscope 1 and to reduce the power consumption of the endoscope 1.

Figure 5:
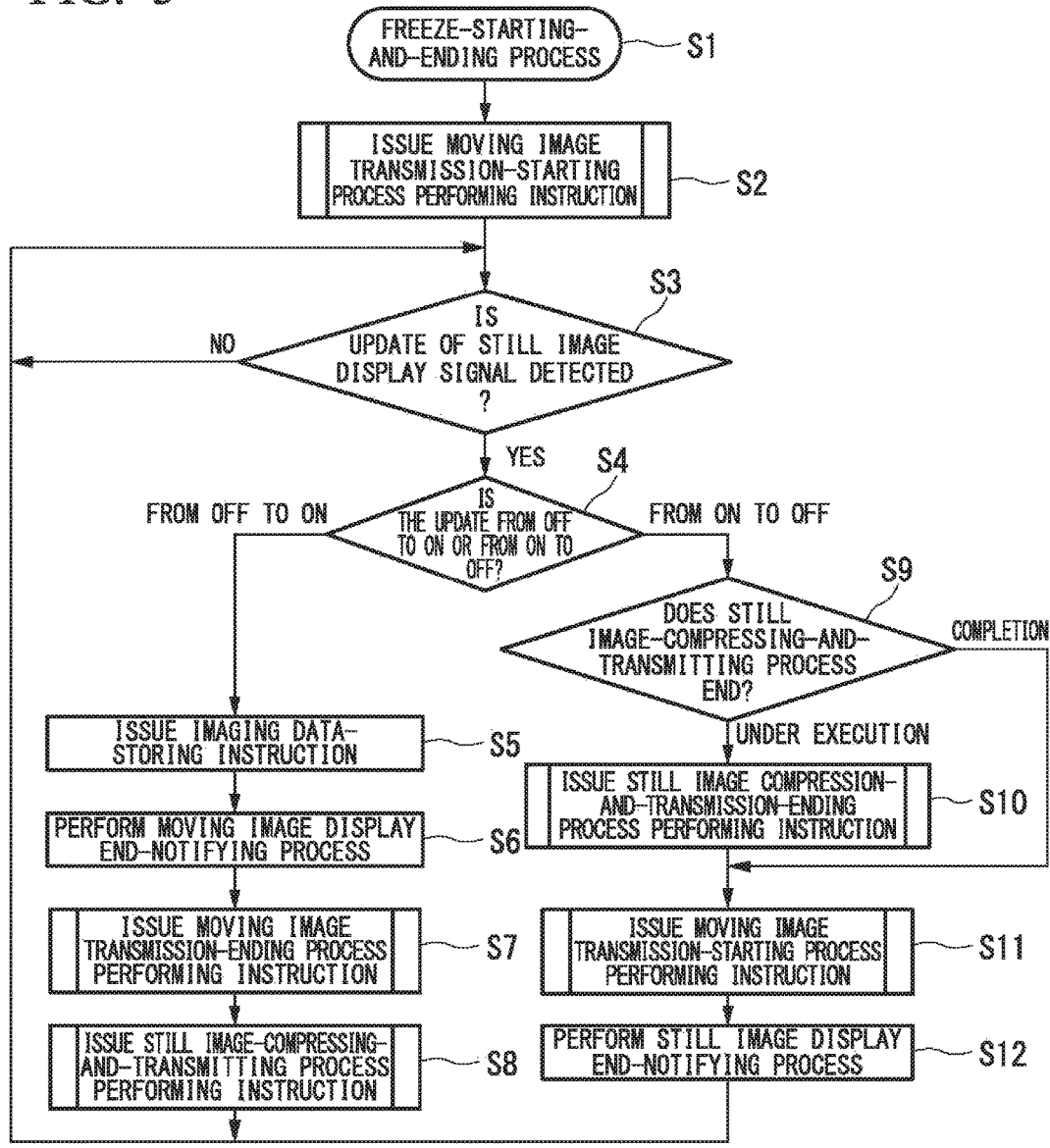
FIG. 5 is a flowchart illustrating an example of an operation of an endoscope according to the first embodiment of the present invention.
Figure 6:
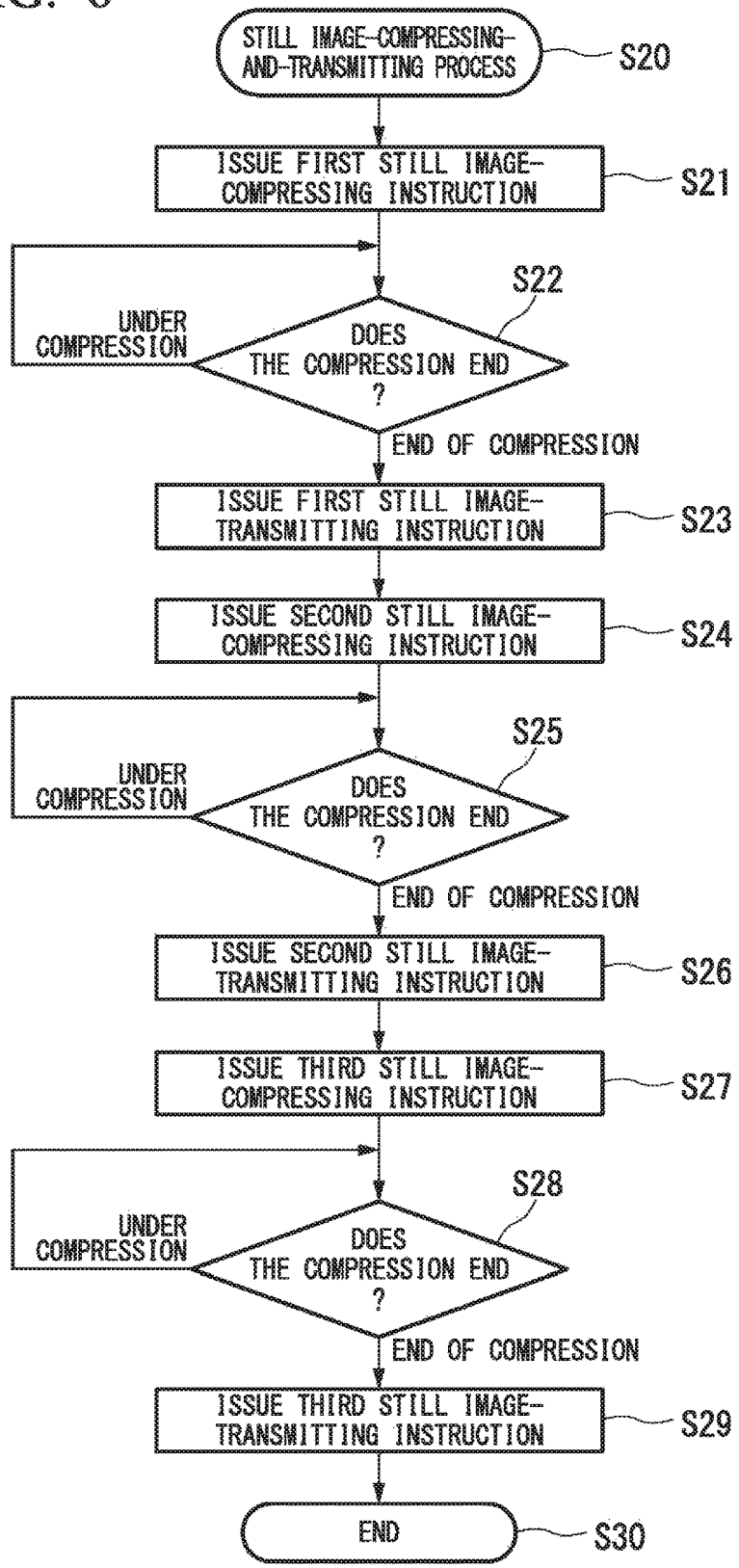
FIG. 6 is a flowchart illustrating an example of the operation of the endoscope according to the first embodiment of the present invention.
Figure 7:
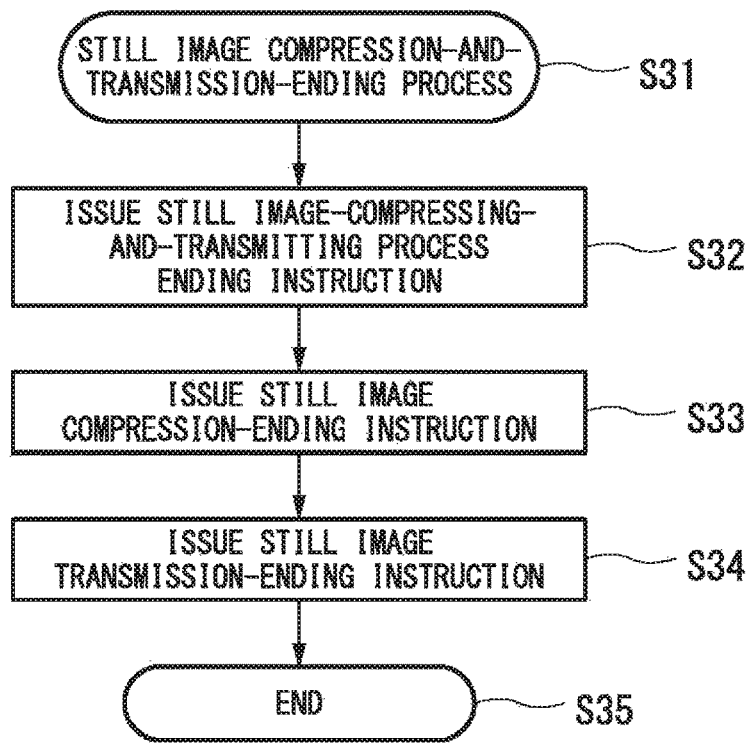
FIG. 7 is a flowchart illustrating an example of the operation of the endoscope according to the first embodiment of the present invention.
Figure 8:
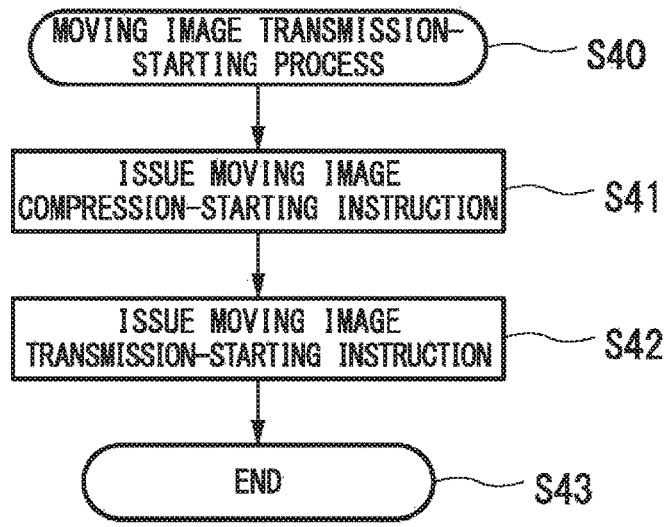
FIG. 8 is a flowchart illustrating an example of the operation of the endoscope according to the first embodiment of the present invention.
Figure 9:
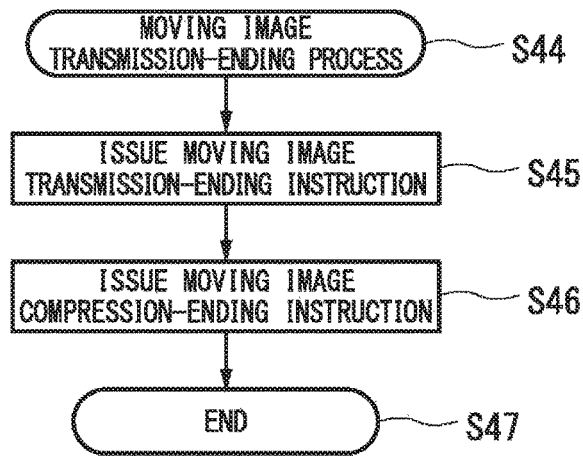
FIG. 9 is a flowchart illustrating an example of the operation of the endoscope according to the first embodiment of the present invention.

Details of the processes relevant to a freeze start and a freeze end will be described below with reference to FIGS. 5 to 9. FIG. 5 illustrates an example of a flow of a freeze-starting-and-ending process (S1) which is performed by the endoscope control unit 10 of the endoscope 1. FIG. 6 illustrates an example of a flow of a still image-compressing-and-transmitting process (S20) which is performed by the endoscope control unit 10 of the endoscope 1. FIG. 7 illustrates an example of a flow of a still image compression-and-transmission-ending process (S31) which is performed by the endoscope control unit 10 of the endoscope 1. FIG. 8 illustrates an example of a flow of a moving image transmission-starting process (S40) which is performed by the endoscope control unit 10 of the endoscope 1. FIG. 9 illustrates an example of a flow of a moving image transmission-ending process (S44) which is performed by the endoscope control unit 10 of the endoscope 1.

The processes illustrated in FIGS. 5 to 9 are constituted as independent processes (tasks). A management program (an operating system (OS)) controls performing the processes. Accordingly, another process is executable while each process is in a "standby" state. When a plurality of processes is executable, a process having higher priority is performed. A method of performing a task under the control of the OS is known and thus description of the task performing method will not be made.

As illustrated in FIG. 5, the following process is performed in the freeze-starting-and-ending process (S1). First, the endoscope control unit 10 issues a moving image transmission-starting process performing instruction (S2). Issuing of the moving image transmission-starting process performing instruction (S2) is a process which instructs to perform the moving image transmission-starting process (S40) illustrated in FIG. 8.

The freeze-starting-and-ending process (S1) and the moving image transmission-starting process (S40) are managed as different tasks by the OS. Accordingly, the freeze-starting-and-ending process (S1) and the moving image transmission-starting process (S40) can be performed in parallel. A priority level of the freeze-starting-and-ending process (S1) is 1, and a priority level of the moving image transmission-starting process (S40) is 5. Since the priority level of the freeze-starting-and-ending process (S1) is set to be higher than the priority level of the moving image transmission-starting process (S40), the endoscope control unit 10 performs an update-detecting process (S3) of the still image display signal 12 after the moving image transmission-starting process performing instruction (S2) is issued but before the moving image transmission-starting process (S40) is performed.

In the update-detecting process (S3) of the still image display signal 12, the endoscope control unit 10 monitors the still image display signal 12 from the freeze-instructing unit 9 and detects an update of the still image display signal 12. When the still image display signal 12 is not updated, the endoscope control unit 10 performs the update-detecting process (S3) of the still image display signal 12 again after a predetermined period passes. That is, when the still image display signal 12 is not updated, the update-detecting process (S3) of the still image display signal 12 is performed with a predetermined cycle. In this case, the freeze-starting-and-ending process (S1) is in a standby state. When the freeze-starting-and-ending process (S1) is in the standby state, the moving image transmission-starting process (S40) which is executable is performed.

As illustrated in FIG. 8, the following process is performed in the moving image transmission-starting process (S40). First, the endoscope control unit 10 causes the moving image-compressing unit 5 to start a moving image-compressing process in response to a moving image compression-starting instruction (S41). Accordingly, the moving image-compressing unit 5 starts the moving image-compressing process.

Subsequently, the endoscope control unit 10 issues a moving image transmission-starting instruction (S42). In the moving image transmission-starting instruction (S42), the endoscope control unit 10 causes the data-selecting unit 7 to select the moving image data which is generated by the moving image-compressing unit 5 performing the moving image compression on the imaging data and causes the transmission unit 8 to transmit the selected moving image data in a wireless manner. Accordingly, the data-selecting unit 7 selects the moving image data. The transmission unit 8 transmits the selected moving image data to the display device 13 in a wireless manner.

When the moving image transmission-starting instruction (S42) is issued, the moving image transmission-starting process (S40) ends (S43). After the moving image transmission-starting process (S40) ends, the endoscope control unit 10 performs the update-detecting process (S3) of the still image display signal 12.

When an operator of the endoscope 1 issues a freeze instruction, the freeze-instructing unit 9 generates the still image display signal 12 in the ON state. Accordingly, the still image display signal 12 is updated from the OFF state to the ON state. This update is detected through the update-detecting process (S3) of the still image display signal 12.

When the still image display signal 12 is updated, the endoscope control unit 10 performs an update details determining process (S4) on the still image display signal 12. When the still image display signal 12 is switched from the OFF state and the ON state, the endoscope control unit 10 issues an imaging data-storing instruction (S5) to start the still image display. In the imaging data-storing instruction (S5), the endoscope control unit 10 instructs the data storage unit 4 to store imaging data for still image display. Accordingly, the data storage unit 4 stores the imaging data generated by the imaging unit 2 by capturing an image as storage data. That is, the data storage unit 4 stores the imaging data at the beginning of the time at which the still image display signal 12 is switched from the OFF state to the ON state.

Subsequently, the endoscope control unit 10 performs a moving image display end-notifying process (S6). In the moving image display end-notifying process (S6), the endoscope control unit 10 notifies the display device 13 of switching from the moving image display to the still image display. In the moving image display end-notifying process (S6), the switching is notified using the management data. The endoscope control unit 10 causes the transmission unit 8 to transmit the management data in a wireless manner. Accordingly, the transmission unit 8 transmits the management data to the display device 13 in a wireless manner. The management data transmitted from the transmission unit 8 in a wireless manner is received by the reception unit 14 of the display device 13. The received management data is output to the display device control unit 17. The display device control unit 17 performs a process of stopping (freezing) an update of the moving image under display and a process of switching the display screen of the display monitor 18 to a still image display screen. A final image of the moving image is displayed on the still image display screen immediately after the screen is switched. At a time at which the still image data in the first still image format is received, the image displayed on the still image display screen is switched from the moving image to the still image.

Subsequently, the endoscope control unit 10 issues a moving image transmission-ending process performing instruction (S7). The moving image transmission-ending process performing instruction (S7) is a process of instructing to perform a moving image transmission-ending process (S44) illustrated in FIG. 9.

The freeze-starting-and-ending process (S1) and the moving image transmission-ending process (S44) are managed as different tasks by the OS. Accordingly, the freeze-starting-and-ending process (S1) and the moving image transmission-ending process (S44) can be performed in parallel. The priority level of the freeze-starting-and-ending process (S1) is 1, and a priority level of the moving image transmission-ending process (S44) is 3. Since the priority level of the freeze-starting-and-ending process (S1) is set to be higher than the priority level of the moving image transmission-ending process (S44), the endoscope control unit 10 issues a still image-compressing-and-transmitting process performing instruction (S8) after issuing the moving image transmission-ending process performing instruction (S7) but before performing the moving image transmission-ending process (S44). The still image-compressing-and-transmitting process performing instruction (S8) is a process of instructing to perform of a still image-compressing-and-transmitting process (S20) illustrated in FIG. 6.

The freeze-starting-and-ending process (S1) and the still image-compressing-and-transmitting process (S20) are managed as different tasks by the OS. Accordingly, the freeze-starting-and-ending process (S1) and the still image-compressing-and-transmitting process (S20) can be performed in parallel. The priority level of the freeze-starting-and-ending process (S1) is 1, and a priority level of the still image-compressing-and-transmitting process (S20) is 4. Since the priority level of the freeze-starting-and-ending process (S1) is set to be higher than the priority level of the still image-compressing-and-transmitting process (S20), the endoscope control unit 10 performs the update-detecting process (S3) of the still image display signal 12 after issuing the still image-compressing-and-transmitting process performing instruction (S8) but before performing the still image-compressing-and-transmitting process (S20). As described above, since the update-detecting process (S3) of the still image display signal 12 is performed with a predetermined cycle, the freeze-starting-and-ending process (S1) is in the standby state.

When the freeze-starting-and-ending process (S1) is in the standby state, the moving image transmission-ending process (S44) which is executable and which has the highest priority level is performed. As illustrated in FIG. 9, the following process is performed in the moving image transmission-ending process (S44). First, the endoscope control unit 10 causes the transmission unit 8 to stop transmitting the moving image data through a moving image transmission-ending instruction (S45). Accordingly, the transmission unit 8 stops transmitting the moving image data.

Subsequently, the endoscope control unit 10 causes the moving image-compressing unit 5 to stop a moving image-compressing process. Accordingly, the moving image-compressing unit 5 stops the moving image-compressing process. When a moving image compression-ending instruction (S46) is performed, the moving image transmission-ending process (S44) ends (S47).

Subsequently, the still image-compressing-and-transmitting process (S20) which is executable is performed. The still image-compressing-and-transmitting process (S20) is a process of updating a still image compression parameter sequentially from a parameter corresponding to a first still image format to a parameter corresponding to a third still image format, generating still image data, and transmitting the generated still image data.

As illustrated in FIG. 6, the following process is performed in the still image-compressing-and-transmitting process (S20). First, the endoscope control unit 10 issues a first still image-compressing instruction (S21). In the first still image-compressing instruction (S21), the endoscope control unit 10 causes the image quality control unit 11 to set the still image compression parameter corresponding to the first still image format and causes the still image-compressing unit 6 to start a still image-compressing process. Accordingly, the image quality control unit 11 sets the still image compression parameter corresponding to the first still image format in the still image-compressing unit 6. The still image-compressing unit 6 starts the still image-compressing process.

Subsequently, the endoscope control unit 10 detects a state of the still image-compressing process which is performed by the still image-compressing unit 6 through a processing state-determining process (S22). While the still image-compressing process is performed, the processing state-determining process (S22) is repeatedly performed. When an end of the still image-compressing process is detected, the endoscope control unit 10 issues a first still image-transmitting instruction (S23). In the first still image-transmitting instruction (S23), the endoscope control unit 10 causes the data-selecting unit 7 to select first still image data which is generated by the still image-compressing unit 6 performing the still image-compressing process on the storage data and causes the transmission unit 8 to transmit the selected first still image data. Accordingly, the data-selecting unit 7 selects the first still image data. The transmission unit 8 transmits the selected first still image data to the display device 13. The first still image data is data which is generated by the still image-compressing process being performed on the storage data output from the data storage unit 4 using the still image compression parameter corresponding to the first still image format.

Subsequently, the endoscope control unit 10 issues a second still image-compressing instruction (S24). In the second still image-compressing instruction (S24), the endoscope control unit 10 causes the image quality control unit 11 to set the still image compression parameter corresponding to the second still image format and causes the still image-compressing unit 6 to start the still image-compressing process. Accordingly, the image quality control unit 11 sets the still image compression parameter corresponding to the second still image format in the still image-compressing unit 6. The still image-compressing unit 6 starts the still image-compressing process. The still image-compressing process on second still image data is started while transmitting the first still image data.

Subsequently, the endoscope control unit 10 detects a state of the still image-compressing process which is performed by the still image-compressing unit 6 through a processing state-determining process (S25). While the still image-compressing process is performed, the processing state-determining process (S25) is repeatedly performed. When an end of the still image-compressing process is detected, the endoscope control unit 10 issues a second still image-transmitting instruction (S26). In the second still image-transmitting instruction (S26), the endoscope control unit 10 causes the data-selecting unit 7 to select the second still image data which is generated by the still image-compressing unit 6 performing the still image-compressing process on the storage data and causes the transmission unit 8 to transmit the selected second still image data. Accordingly, the data-selecting unit 7 selects the second still image data. The transmission unit 8 transmits the selected second still image data to the display device 13 in a wireless manner. The second still image data is data which is generated by the still image-compressing process being performed on the storage data output from the data storage unit 4 using the still image compression parameter corresponding to the second still image format.

Subsequently, the endoscope control unit 10 issues a third still image-compressing instruction (S27). In the third still image-compressing instruction (S27), the endoscope control unit 10 causes the image quality control unit 11 to set the still image compression parameter corresponding to the third still image format and causes the still image-compressing unit 6 to start the still image-compressing process. Accordingly, the image quality control unit 11 sets the still image compression parameter corresponding to the third still image format in the still image-compressing unit 6. The still image-compressing unit 6 starts the still image-compressing process. The still image-compressing process on the third still image data is started while transmitting the second still image data.

Subsequently, the endoscope control unit 10 detects a state of the still image-compressing process which is performed by the still image-compressing unit 6 through a processing state-determining process (S28). While the still image-compressing process is performed, the processing state-determining process (S28) is repeatedly performed. When an end of the still image-compressing process is detected, the endoscope control unit 10 issues a third still image-transmitting instruction (S29). In the third still image-transmitting instruction (S29), the endoscope control unit 10 causes the data-selecting unit 7 to select third still image data which is generated by the still image-compressing unit 6 performing the still image-compressing process on the storage data and causes the transmission unit 8 to transmit the selected third still image data. Accordingly, the data-selecting unit 7 selects the third still image data. The transmission unit 8 transmits the selected third still image data to the display device 13 in a wireless manner. The third still image data is data which is generated by the still image-compressing process being performed on the storage data output from the data storage unit 4 using the still image compression parameter corresponding to the third still image format.

When the third still image-transmitting instruction (S29) is issued, the still image-compressing-and-transmitting process (S20) ends (S30). By the above-mentioned flow, the still image-compressing unit 6 performs the still image-compressing process on the storage data and generates a plurality of pieces of still image data, that is, the first still image data, the second still image data, and the third still image data. By the above-mentioned flow, the image quality of still image data generated later becomes higher. That is, the image quality of the second still image data is higher than the image quality of the first still image data. The image quality of the third still image data is higher than the image quality of the second still image data. Three types of still image data generated from the same imaging data are transmitted in the order of the first still image data, the second still image data, and the third still image data.

When it is determined in the update details determining process (S4) of the still image display signal 12 that the still image display signal 12 is switched from the ON state to the OFF state, a display mode is switched from a still image display to a moving image display in this way. At the time at which a switching instruction is issued, the endoscope control unit 10 determines whether the still image-compressing-and-transmitting process (S20) is being performed by the performing state-determining process (S9) of the still image-compressing-and-transmitting process.

When the still image-compressing-and-transmitting process (S20) ends, the endoscope control unit 10 issues a moving image transmission-starting process performing instruction (S11). The moving image transmission-starting process performing instruction (S11) is a process of instructing to perform the moving image transmission-starting process (S40) illustrated in FIG. 8.

When the still image-compressing-and-transmitting process (S20) is being performed, the endoscope control unit 10 issues a still image compression-and-transmission-ending process performing instruction (S10). The still image compression-and-transmission-ending process performing instruction (S10) is a process of instructing to perform the still image compression-and-transmission-ending process (S31) illustrated in FIG. 7.

The freeze-starting-and-ending process (S1) and the still image compression-and-transmission-ending process (S31) are managed as different tasks by the OS. Accordingly, the freeze-starting-and-ending process (S1) and the still image compression-and-transmission-ending process (S31) can be performed in parallel. The priority level of the freeze-starting-and-ending process (S1) is 1, and a priority level of the still image compression-and-transmission-ending process (S31) is 2. Since the priority level of the freeze-starting-and-ending process (S1) is set to be higher than the priority level of the still image compression-and-transmission-ending process (S31), the endoscope control unit 10 issues the moving image transmission-starting process performing instruction (S11) after issuing the still image compression-and-transmission-ending process performing instruction (S10) and before performing the still image compression-and-transmission-ending process (S31). The still image compression starting process performing instruction (S11) is the process of instructing to perform the moving image transmission-starting process (S40) illustrated in FIG. 8.

The freeze-starting-and-ending process (S1) and the moving image transmission-starting process (S40) are managed as different tasks by the OS. Accordingly, the freeze-starting-and-ending process (S1) and the moving image transmission-starting process (S40) can be performed in parallel. The priority level of the freeze-starting-and-ending process (S1) is 1, and the priority level of the moving image transmission-starting process (S40) is 5. Since the priority level of the freeze-starting-and-ending process (S1) is set to be higher than the priority level of the moving image transmission-starting process (S40), the endoscope control unit 10 performs a still image display end-notifying process (S12) after issuing the moving image transmission-starting process performing instruction (S11) and before performing the moving image transmission-starting process (S40).

In the still image display end-notifying process (S12), the endoscope control unit 10 notifies the display device 13 of switching from the still image display to the moving image display. In the still image display end-notifying process (S12), the switching is notified using the management data. The management data transmitted from the transmission unit 8 in a wireless manner is received by the reception unit 14 of the display device 13. The received management data is output to the display device control unit 17. The display device control unit 17 performs a process of switching the screen displayed on the display monitor 18 to a moving image display screen on the basis of the management data. A still image is displayed on the moving image display screen immediately after the screen is switched. At the time at which the moving image data is received, the image displayed on the moving image display screen is switched from the still image to the moving image.

After the still image display end-notifying process (S12) is performed, the update-detecting process (S3) of the still image display signal 12 is performed. As described above, since the update-detecting process (S3) of the still image display signal 12 is performed with a predetermined cycle, the freeze-starting-and-ending process (S1) is in the standby state.

At this time, the still image compression-and-transmission-ending process (S31) having the priority level of 2 and the moving image transmission-starting process (S40) having the priority level of 5 are executable. The still image compression-and-transmission-ending process (S31) having the higher priority level is performed earlier than the moving image transmission-starting process (S40).

As illustrated in FIG. 7, the following process is performed in the still image compression-and-transmission-ending process (S31). First, the endoscope control unit 10 stops the still image-compressing-and-transmitting process (S20) by a still image-compressing-and-transmitting process ending instruction (S32). Subsequently, the endoscope control unit 10 causes the still image-compressing unit 6 to stop the still image-compressing process by a still image compression-ending instruction (S33). Accordingly, the still image-compressing unit 6 stops the still image-compressing process.

Subsequently, the endoscope control unit 10 causes the transmission unit 8 to stop transmitting the still image data by a still image transmission-ending instruction (S34). Accordingly, the transmission unit 8 stops transmitting the still image data. When the still image transmission-ending instruction (S34) is issued, the still image compression-and-transmission-ending process (S31) ends (S35).

After the still image compression-and-transmission-ending process (S31) ends, the endoscope control unit 10 performs the moving image transmission-starting process (S40). The moving image transmission-starting process (S40) has been described above and thus) will not be repeatedly described. After the moving image transmission-starting process (S40) ends, the update-detecting process (S3) of the still image display signal 12 is performed. By the above-mentioned flow, the freeze-starting-and-ending process (S1) is performed.

Details of a process which is performed by the display device 13 will be described below. The management data in this embodiment is transmitted in the moving image display end-notifying process (S6) illustrated in FIG. 5, in the still image display end-notifying process (S12) illustrated in FIG. 5, and at the times immediately before a transmission of a first frame of the moving image data is started and immediately before a transmission of each frame of the still image data is started. The management data transmitted in the moving image display end-notifying process (S6) and the still image display end-notifying process (S12) is used to switch between the moving image display and the still image display. The management data transmitted at the times immediately before the transmission of a first frame of the moving image data is started and immediately before the transmission of each frame of the still image data is started is used to determine the type of image data and to set an image data-processing parameter.

When the management data is transmitted from the endoscope 1, the reception unit 14 of the display device 13 receives the management data. The reception unit 14 outputs the received management data to the display device control unit 17. The display device control unit 17 analyzes details of the management data. The display device control unit 17 sets the parameter corresponding to the image data format in the image-decompressing unit 15 and the image display unit 16.

Figure 10:
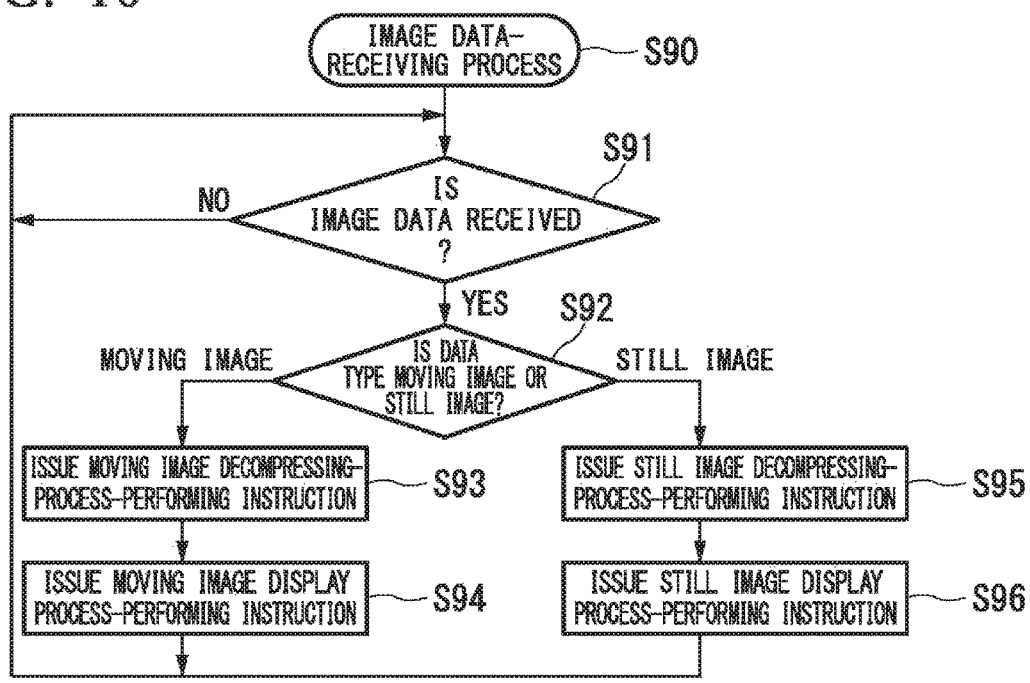
FIG. 10 is a flowchart illustrating an example of the operation of a display device according to the first embodiment of the present invention.

Details of the processes of receiving and displaying image data, which are performed by the display device 13, will be described below with reference to FIG. 10. FIG. 10 illustrates an example of a flow of an image data-receiving process (S90) which is performed by the display device control unit 17 of the display device 13. In FIG. 10, the management data-receiving process is not illustrated. As illustrated in FIG. 10, the following process is performed in the image data-receiving process (S90).

First, the display device control unit 17 waits for receiving image data (S91). When moving image data or still image data is transmitted from the endoscope 1 in a wireless manner, the display device control unit 17 causes the reception unit 14 to receive the moving image data or the still image data transmitted from the endoscope 1 in a wireless manner. Accordingly, the reception unit 14 receives the moving image data or the still image data.

When the moving image data or the still image data is received, the display device control unit 17 performs a data type determining process (S92). In the data type determining process (S92), the display device control unit 17 determines the type of the received image data on the basis of the management data which is received before the image data is received. When the type of the received image data is the moving image data, a parameter corresponding to processing of the moving image is set in the image-decompressing unit 15 and the image display unit 16 immediately before the first frame of the moving image data is received. The process is performed on the basis of this parameter.

The display device control unit 17 causes the image-decompressing unit 15 to perform a moving image data-decompressing process in response to a moving image decompressing-process-performing instruction (S93). Accordingly, the image-decompressing unit 15 performs a decompressing process on the moving image data received by the reception unit 14 and generates display data. Subsequently, the display device control unit 17 causes the image display unit 16 to perform a moving image display process in response to a moving image display process-performing instruction (S94). Accordingly, the image display unit 16 performs a display process using the display data. As a result, a moving image is displayed on the display monitor 18. After the moving image display process-performing instruction (S94) is issued, the display device control unit 17 waits for receiving image data of a next frame (S91).

When the type of the received image data is the still image data, a parameter corresponding to processing of a still image is set in the image-decompressing unit 15 and the image display unit 16, immediately before the frames of the still image data are received. The process is performed on the basis of this parameter.

The display device control unit 17 causes the image-decompressing unit 15 to perform a still image data-decompressing process in response to a still image decompressing-process-performing instruction (S95). Accordingly, the image-decompressing unit 15 performs a decompressing process on the still image data received by the reception unit 14 and generates display data. Subsequently, the display device control unit 17 causes the image display unit 16 to perform the still image display process in response to a still image display process-performing instruction (S96). Accordingly, the image display unit 16 performs a display process using the display data. Accordingly, a still image is displayed on the display monitor 18. After the still image display process-performing instruction (S96) is issued, the display device control unit 17 waits for receiving image data of a next frame (S91).

In this embodiment, three types of data of the first still image data, the second still image data, and the third still image data are transmitted in the order in which the still image data is generated by the still image-compressing unit 6. Accordingly, the image-decompressing unit 15 generates a plurality of pieces of display data in the order in which the plurality of pieces of still image data are generated in the process of decompressing the plurality of pieces of still image data.

In FIG. 1, the data bus 3 and the display monitor 18 are not an essential configuration of the wireless endoscope system according to this embodiment. Among the processes illustrated in FIGS. 5 to 9, the processes other than the update-detecting process (S3) of the still image display signal 12 illustrated in FIG. 5, the imaging data storage instruction (S5) illustrated in FIG. 5, the still image-compressing-and-transmitting process (S20) illustrated in FIG. 6, and the moving image transmission-starting process (S40) illustrated in FIG. 8 are not essential processes of the wireless endoscope system according to this embodiment. Details of the processes illustrated in FIGS. 6 to 9 can be appropriately changed.

According to this embodiment, the wireless endoscope system includes: an imaging unit 2 that captures an image and generates imaging data; a freeze-instructing unit 9 that generates a still image display signal 12 relevant to execution of still image display; a data storage unit 4 that stores the imaging data as storage data at a time at which the still image display signal 12 is switched from a first state indicating execution of moving image display to a second state indicating execution of still image display; a moving image-compressing unit 5 that performs a moving image-compressing process on the imaging data and generates moving image data; a still image-compressing unit 6 that performs a still image-compressing process on the storage data and generates a plurality of pieces of still image data; an image quality control unit 11 that controls image quality of the plurality of pieces of still image data such that the image quality of the piece of still image data generated later among the plurality of pieces of still image data becomes higher; a data-selecting unit 7 that selects the moving image data when the still image display signal 12 is in the first state and sequentially selects the plurality of pieces of still image data in the order in which the plurality of pieces of still image data are generated when the still image display signal 12 is in the second state; a transmission unit 8 that transmits the moving image data or the plurality of pieces of still image data selected by the data-selecting unit 7 in a wireless manner; a reception unit 14 that receives the moving image data or the plurality of pieces of still image data transmitted from the transmission unit 8 in a wireless manner; an image-decompressing unit 15 that performs a decompressing process on the moving image data or the plurality of pieces of still image data received by the reception unit 14 and generates display data, the image-decompressing unit generating a plurality of pieces of display data in the order in which the plurality of pieces of still image data are generated in the decompressing process on the plurality of pieces of still image data; and an image display unit 16 that performs a display process based on the display data.

According to this embodiment, the endoscope 1 includes: an imaging unit 2 that captures an image and generates imaging data; a freeze-instructing unit 9 that generates a still image display signal 12 relevant to execution of still image display; a data storage unit 4 that stores the imaging data as storage data at a time at which the still image display signal 12 is switched from a first state indicating execution of moving image display to a second state indicating execution of still image display; a moving image-compressing unit 5 that performs a moving image-compressing process on the imaging data and generates moving image data; a still image-compressing unit 6 that performs a still image-compressing process on the storage data and generates a plurality of pieces of still image data; an image quality control unit 11 that controls image quality of the plurality of pieces of still image data such that the image quality of the piece of still image data generated later among the plurality of pieces of still image data becomes higher; a data-selecting unit 7 that selects the moving image data when the still image display signal 12 is in the first state and sequentially selects the plurality of pieces of still image data in the order in which the plurality of pieces of still image data are generated when the still image display signal 12 is in the second state; and a transmission unit 8 that transmits the moving image data or the plurality of pieces of still image data selected by the data-selecting unit 7 in a wireless manner.

According to this embodiment, the display device 13 includes: a reception unit 14 that receives moving image data or a plurality of pieces of still image data transmitted from an endoscope 1 in a wireless manner; an image-decompressing unit 15 that performs a decompressing process on the moving image data or the plurality of pieces of still image data received by the reception unit 14 and generates display data, the image-decompressing unit generating a plurality of pieces of display data in the order in which the plurality of pieces of still image data are generated in the decompressing process on the plurality of pieces of still image data; and an image display unit 16 that performs a display process based on the display data.

According to this embodiment, the image transmission method includes: a step (S3) of generating a still image display signal 12 relevant to execution of still image display by a freeze-instructing unit 9; a step (S5) of storing imaging data which is generated by an imaging unit 2 by capturing an image as storage data at a time at which the still image display signal 12 is switched from a first state indicating execution of moving image display to a second state indicating execution of still image display; a step (S41) of performing a moving image-compressing process on the imaging data and to generate moving image data by a moving image-compressing unit 5; a step (S21, S24, S27) of causing a still image-compressing unit 6 to perform a still image-compressing process on the storage data by a still image-compressing unit 6 to generate a plurality of pieces of still image data such that the image quality of the piece of still image data generated later among the plurality of pieces of still image data becomes higher; a step (842) of transmitting the moving image data in a wireless manner by a transmission unit 8 when the still image display signal 12 is in the first state; and a step (S23, S26, S29) of transmitting the plurality of pieces of still image data in a wireless manner in the order in which the plurality of pieces of still image data are generated by the transmission unit 8 when the still image display signal 12 is in the second state.

According to this embodiment, the image display method includes: a step (S91) of receiving moving image data or a plurality of pieces of still image data transmitted from an endoscope 1 in a wireless manner by a reception unit 14; a step (S93, S95) of performing a decompressing process on the moving image data or the plurality of pieces of still image data received by the reception unit 14 and to generate display data, and generating a plurality of pieces of display data in the order in which the plurality of pieces of still image data are generated in the decompressing process on the plurality of pieces of still image data by an image-decompressing unit 15; and a step (S94, S96) of performing a display process based on the display data by an image display unit.

According to this embodiment, the program causes a computer of an endoscope 1 to perform: a step (S3) of detecting a still image display signal 12 relevant to execution of still image display which is generated by a freeze-instructing unit 9; a step (S5) of causing a data storage unit 4 to store imaging data which is generated by an imaging unit 2 by capturing an image as storage data at a timing at which the still image display signal 12 is switched from a first state indicating execution of moving image display to a second state indicating execution of still image display; a step (S41) of causing a moving image-compressing unit 5 to perform a process of performing a moving image-compressing process on the imaging data and generating moving image data; a step (S21, S24, S27) of causing a still image-compressing unit 6 to perform a process of performing a still image-compressing process on the storage data and generating a plurality of pieces of still image data such that the image quality of the piece of still image data generated later among the plurality of pieces of still image data becomes higher; a step (S42) of causing a transmission unit 8 to transmit the moving image data in a wireless manner when the still image display signal 12 is in the first state; and a step (S23, S26, S29) of causing the transmission unit 8 to transmit the plurality of pieces of still image data in a wireless manner in the order in which the plurality of pieces of still image data are generated when the still image display signal is in the second state.

According to this embodiment, the program causes a computer to perform: a step (S91) of causing a reception unit 14 to receive moving image data or a plurality of pieces of still image data transmitted from an endoscope 1 in a wireless manner; a step (S93, S95) of causing an image-decompressing unit 15 to perform a decompressing process on the moving image data or the plurality of pieces of still image data received by the reception unit 14 and to generate display data, and causing the image-decompressing unit to generate a plurality of pieces of display data in the order in which the plurality of pieces of still image data are generated in the decompressing process on the plurality of pieces of still image data; and a step (S94, S96) of causing an image display unit 16 to perform a display process based on the display data.

According to this embodiment, image quality of a plurality of pieces of still image data is controlled such that image quality of the still image data generated later becomes higher. Accordingly, it is possible to decrease an initial display delay of a still image, to decrease a size of an endoscope 1, and to reduce power consumption of the endoscope 1.

(Second Embodiment)

Next, a second embodiment of the present invention will be described below. In this embodiment, an automatic storage function, a display quality-selecting function, and a preferential display function are added to the wireless endoscope system according to the first embodiment. The automatic storage function is a function of automatically storing a still image having image quality equal to or more than predetermined image quality as a target image. The display quality-selecting function is a function of selecting an execution order of a still image-compressing process. The preferential display function is a function of preferentially displaying a still image with high image quality.

Figure 11:
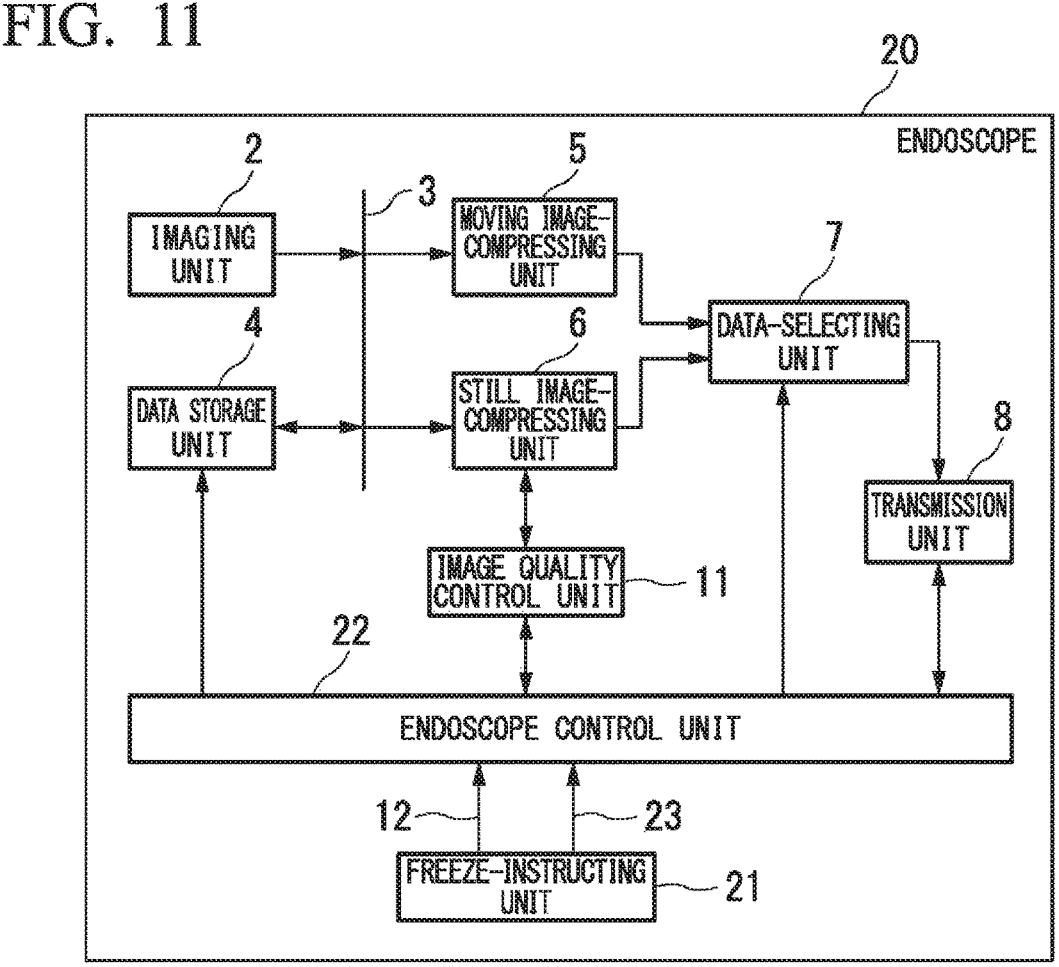
FIG. 11 is a block diagram illustrating an example of a configuration of an endoscope according to a second embodiment of the present invention.

In this embodiment, the endoscope 1 illustrated in FIG. 1 is replaced with an endoscope 20 illustrated in FIG. 11. FIG. 11 illustrates an example of a configuration of the endoscope 20. As illustrated in FIG. 11, the endoscope 20 includes an imaging unit 2, a data bus 3, a data storage unit 4, a moving image-compressing unit 5, a still image-compressing unit 6, a data-selecting unit 7, a transmission unit 8, an image quality control unit 11, a freeze-instructing unit 21, and an endoscope control unit 22. Since the imaging unit 2, the data bus 3, the data storage unit 4, the moving image-compressing unit 5, the still image-compressing unit 6, the data-selecting unit 7, the transmission unit 8, and the image quality control unit 11 have been described above, description of the elements will not be repeated. In this embodiment, the freeze-instructing unit 9 in the endoscope 1 illustrated in FIG. 1 is replaced with the freeze-instructing unit 21. In this embodiment, the endoscope control unit 10 in the endoscope 1 illustrated in FIG. 1 is replaced with the endoscope control unit 22.

The freeze-instructing unit 21 has a function of the freeze-instructing unit 9 in the first embodiment and a function of generating a high definition request signal 23 relevant to a request for still image data having predetermined highest image quality. That is, the freeze-instructing unit 21 according to this embodiment serves as a high image quality-requesting unit that generates the high definition request signal 23. The high definition request signal 23 is used to implement the preferential display function.

In the freeze-instructing unit 21, the button for outputting the still image display signal 12 is replaced with a two-step push button. When the button is pushed to a first step, the still image display signal 12 is switched to an ON state. When the button is pushed to a second step, the high definition request signal 23 is switched to an ON state. The freeze-instructing unit 9 and the high image quality-requesting unit that generates the high definition request signal 23 may be separately provided.

The endoscope control unit 22 performs a still image-compressing-and-transmitting process (S70) different from the still image-compressing-and-transmitting process (S20) in the first embodiment. Details of the still image-compressing-and-transmitting process (S70) will be described later.

Figure 12:
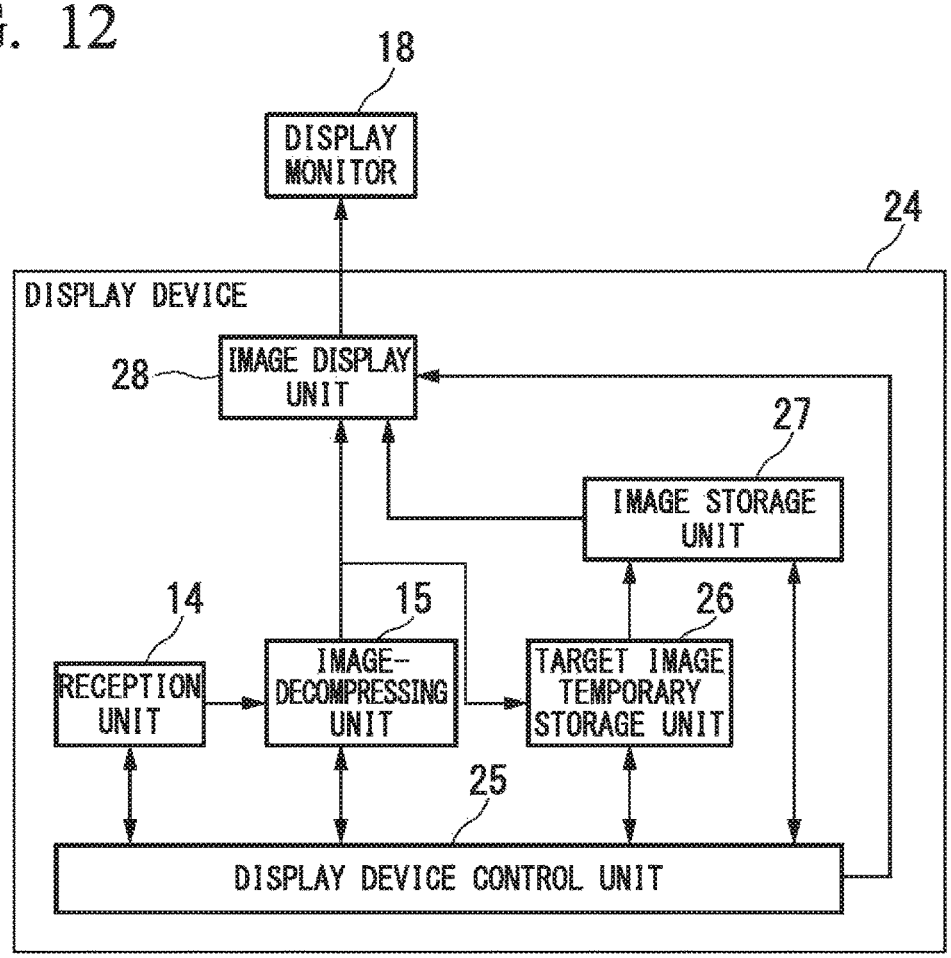
FIG. 12 is a block diagram illustrating an example of a configuration of a display device according to the second embodiment of the present invention.

In this embodiment, the display device 13 illustrated in FIG. 1 is replaced with a display device 24 illustrated in FIG. 12. FIG. 12 illustrates an example of a configuration of the display device 24. The configuration and the operation of the display device 24 will be described below with reference to FIG. 12.

As illustrated in FIG. 12, the display device 24 includes a reception unit 14, an image-decompressing unit 15, a display device control unit 25 (the target image-designating unit, the control unit), a target image temporary storage unit 26, an image storage unit 27, and an image display unit 28. Since the reception unit 14 and the image-decompressing unit 15 have been described above, description of these elements will not be repeated. In this embodiment, the target image temporary storage unit 26 and the image storage unit 27 are added to the display device 13 illustrated in FIG. 1. In this embodiment, the display device control unit 17 of the display device 13 illustrated in FIG. 1 is replaced with the display device control unit 25. In this embodiment, the image display unit 16 of the display device 13 illustrated in FIG. 1 is replaced with the image display unit 28.

The display device control unit 25 additionally has the automatic storage function and the display quality-selecting function. The target image temporary storage unit 26 temporarily stores display data which is automatically stored in the image storage unit 27 as target image data. The target image temporary storage unit 26 includes a volatile storage medium for temporarily storing the display data output from the image-decompressing unit 15. The image storage unit 27 stores the display data corresponding to still image data having image quality equal to or more than predetermined image quality as target image data. The image storage unit 27 includes nonvolatile storage medium for storing the target image data. The image display unit 28 has a function of the image display unit 16 of the display device 13 illustrated in FIG. 1 and a function of performing a display process on the target image data stored in the image storage unit 27.

An operation associated with the automatic storage function is as follows. The display device control unit 25 designates the display data as the target image data when the image quality of the still image data corresponding to the display data generated by the image-decompressing unit 15 at a time immediately before the still image display signal 12 is switched from an ON state (second state) to an OFF state (first state) is equal to or more than predetermined image quality. Since the display data generated by the image-decompressing unit 15 is temporarily stored in the target image temporary storage unit 26, the display data temporarily stored in the target image temporary storage unit 26 is designated as the target image data. The image storage unit 27 stores the display data designated as the target image data.

The time at which the still image display signal 12 is switched from the ON state to the OFF state is notified to the display device 24 using management data for notifying the end of still image display (display switching). The display data which is completely generated by the image-decompressing unit 15 at the time at which the management data is received, that is, the display data temporarily stored in the target image temporary storage unit 26 at the time at which the management data is received, is display data generated by the image-decompressing unit 15 at the time immediately before the still image display signal 12 is switched from the ON state to the OFF state.

An operation associated with the display quality-selecting function is as follows. In this embodiment, the image quality of the still image displayed on the display monitor 18 can be selected by controlling generation of the still image data for each piece of the still image data. The endoscope control unit 22 controls generation of a plurality of pieces of still image data on the basis of a selection table (execution information) indicating whether generation of the plurality of pieces of still image data should be executed. That is, the endoscope control unit 22 determines whether to generate the still image data for each of the plurality of pieces of still image data piece by piece on the basis of the selection table. The endoscope control unit 22 controls generation of the still image data on the basis of the determination result. Details of the selection table will be described later.

An operation associated with the preferential display function is as follows. The freeze-instructing unit 21 generates the high definition request signal 23 relevant to the request for the still image data having predetermined highest image quality. When the high definition request signal 23 is in the ON state, the still image data corresponding to the highest image quality, that is, the third still image data is generated by the preferential display function. When the high definition request signal 23 is in the OFF state, the plurality of pieces of still image data are generated in a predetermined order, similarly to the first embodiment.

Specifically, when the still image display signal 12 is in the ON state (second state) and the high definition request signal 23 is in the ON state (third state) indicating a request for a still image having the highest image quality before the final still image data among plurality of pieces of still image data is generated, the image quality control unit 11 sets the image quality of the still image data to the highest image quality.

Specifically, when the still image display signal 12 is in the ON state (second state) and the high definition request signal 23 is in the OFF state (fourth state) other than the ON state (third state) before the final still image data among plurality of pieces of still image data is generated, the image quality control unit 11 changes the image quality of the plurality of pieces of still image data such that the image quality of the still image data generated later becomes higher and such that the image quality of the final still image data is the highest image quality.

Figure 13:
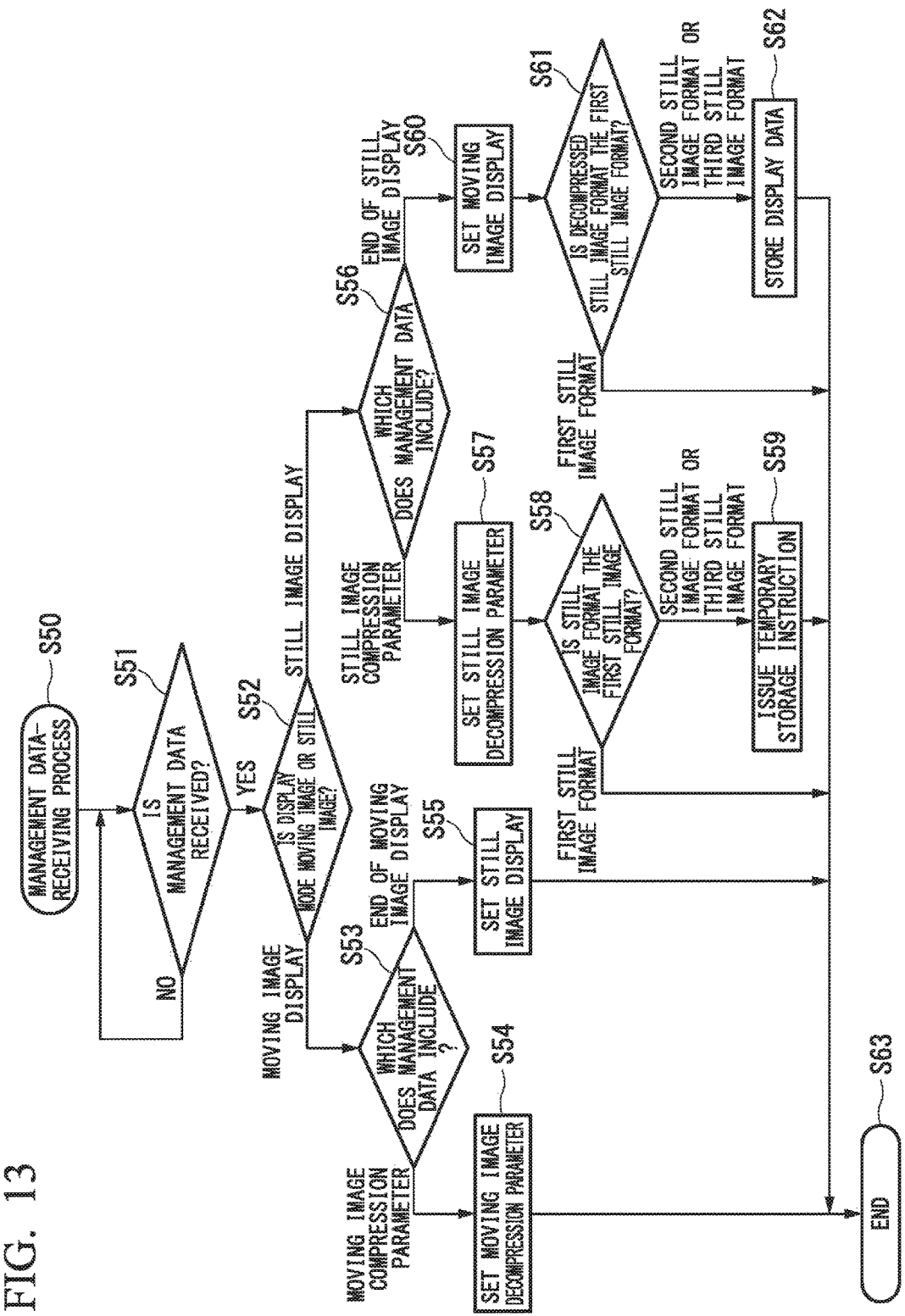
FIG. 13 is a flowchart illustrating an example of an operation of the display device according to the second embodiment of the present invention.

A flow of a target image determining process and a target image storing process, which are associated with the automatic storage function in this embodiment will be described below with reference to FIG. 13. FIG. 13 illustrates an example of a flow of a management data-receiving process (S50) which is performed by the display device control unit 25 of the display device 24.

The management data-receiving process (S50) is a process which is performed by the display device control unit 25 when the reception unit 14 of the display device 24 receives management data from the endoscope 20. Specifically, when the reception unit 14 receives the management data for notifying display end of a moving image or a still image (display switching), the display device control unit 25 instructs the image display unit 28 to switch the display and instructs the image storage unit 27 to store target image data. When the reception unit 14 receives the management data including a still image compression parameter and a parameter indicating a type of image data, the display device control unit 25 sets a still image decompression parameter in the image-decompressing unit 15 and instructs the target image temporary storage unit 26 to temporarily store display data.

The endoscope 20 performs the freeze-starting-and-ending process (S1) illustrated in FIG. 5, similarly to the endoscope 1 illustrated in FIG. 1. The management data in this embodiment is transmitted in the moving image display end-notifying process (S6) illustrated in FIG. 5, in the still image display end-notifying process (S12) illustrated in FIG. 5, and at the times immediately before transmission of a first frame of the moving image data is started and immediately before transmission of each frame of the still image data is started. The management data transmitted in the moving image display end-notifying process (S6) and the still image display end-notifying process (S12) is used to switch the moving image display and the still image display. The management data transmitted at the times immediately before transmission of a first frame of the moving image data is started and immediately before transmission of each frame of the still image data is started is used to determine the parameter for the image data-decompressing process and the target image data.

Detailed description will be made below with reference to FIG. 13. In the management data-receiving process (S50), the display device control unit 25 first waits for receiving the management data (S51). When the management data is transmitted from the endoscope 20 in a wireless manner, the display device control unit 25 causes the reception unit 14 to receive the management data transmitted from the endoscope 20 in a wireless manner. Accordingly, the reception unit 14 receives the management data.

When the management data is received, the display device control unit 25 determines which of the moving image display mode and the still image display mode a current display mode is by a display mode-determining process (S52). The determination is performed on the basis of the management data from the endoscope 20. Specifically, the management data transmitted by the moving image display end-notifying process (S6) illustrated in FIG. 5 is received, the display device control unit 25 stores information indicating that the display mode is the still image display mode. When the management data transmitted by the still image display end-notifying process (S12) is received, the display device control unit 25 stores information indicating that the display mode is the moving image display mode. The display device control unit 25 determines the current display mode on the basis of the information indicating the display mode, which is stored in the display device control unit 25.

When the current display mode is the moving image display mode, the display device control unit 25 determines details of the management data received in S51 by a management data details-determining process (S53). When the moving image compression parameter is included in the management data, the display device control unit 25 performs a moving image decompression parameter-setting process (S54). The moving image decompression parameter-setting process (S54) is a process of setting the moving image decompression parameter in the image-decompressing unit 15.

In the moving image decompression parameter-setting process (S54), the display device control unit 25 notifies the image-decompressing unit 15 of the moving image compression parameter included in the management data. The image-decompressing unit 15 stores the moving image decompression parameter and the still image decompression parameter in advance. When the moving image compression parameter is notified, the image-decompressing unit 15 selects the moving image decompression parameter corresponding to the notified parameter. Accordingly, the moving image decompression parameter is set in the image-decompressing unit 15. When moving image data is received after the moving image decompression parameter is set, the image-decompressing unit 15 performs a decompressing process on the received moving image data using the selected parameter.

When data indicating that the mode to be ended is the moving image display mode is included in the management data, the display device control unit 25 performs a still image display-setting process (S55). In the still image display-setting process (S55), the display device control unit 25 switches the display data generated by the image display unit 28 from the moving image display data to the still image display data by setting the parameter corresponding to the still image display mode in the image display unit 28. The final image of the moving image is displayed on the still image display screen immediately after the switching is performed.

In the display mode-determining process (S52), when the current display mode is the still image display mode, the display device control unit 25 determines details of the management data received in S51 by a management data details determining process (S56). When the still image compression parameter is included in the management data, the display device control unit 25 performs a still image decompression parameter-setting process (S57). The still image decompression parameter-setting process (S57) is a process of setting the still image decompression parameter in the image-decompressing unit 15.

In the still image decompression parameter-setting process (S57), the display device control unit 25 notifies the image-decompressing unit 15 of the still image compression parameter included in the management data. As described above, the image-decompressing unit 15 stores the moving image decompression parameter and the still image decompression parameter in advance. The image-decompressing unit 15 stores the still image decompression parameters corresponding to a plurality of still image formats. When the still image compression parameter is notified, the image-decompressing unit 15 selects the still image decompression parameter corresponding to the notified parameter. Accordingly, the still image decompression parameter is set in the image-decompressing unit 15. When the still image data is received after the still image decompression parameter is set, the image-decompressing unit 15 performs the decompressing process on the received still image data using the selected parameter.

Subsequently, the display device control unit 25 determines the still image format of the received still image data by a still image format-determining process (S58). As described above, the management data including the still image compression parameter is transmitted at the head of each frame of the still image data. Accordingly, the still image compression parameter included in the management data indicates the format of the still image data which is transmitted subsequently to the management data.

In this embodiment, the display data corresponding to the second still image format and the display data corresponding to the third still image format are used as the target image data. When the still image format is the first still image format, a management data-receiving process (S50) ends (S63). When the still image format is the second still image format or the third still image format, the display device control unit 25 issues a temporary storage instruction (S59).

In the temporary storage instruction (S59), the display device control unit 25 instructs the target image temporary storage unit 26 to temporarily store the display data corresponding to the second still image format or the third still image format, which is output from the image-decompressing unit 15, as a target image. When the temporary storage instruction (S59) is issued, the display data stored in the target image temporary storage unit 26 up to that time is deleted and the display data output from the image-decompressing unit 15 is newly stored in the target image temporary storage unit 26. After the temporary storage instruction (S59) is issued, the management data-receiving process (S50) ends (S63).

When data indicating that the mode to be ended is the still image display mode is included in the management data, the display device control unit 25 performs a moving image display-setting process (S60). In the moving image display-setting process (S60), the display device control unit 25 switches the display data generated by the image display unit 28 from the still image display data to the moving image display data by setting the parameter corresponding to the moving image display mode in the image display unit 28. An image corresponding to the still image data which is finally decompressed is displayed on the moving image display screen immediately after the switching is performed.

Subsequently, the display device control unit 25 determines the still image format corresponding to the still image data having been completely subjected to the decompressing process at the time at which the management data is received by a decompressed still image format-determining process (S61). When the still image format is the first still image format, the management data-receiving process (S50) ends (S63). When the still image format is the second still image format or the third still image format, the display device control unit 25 performs a display data-storing process (S62).

In the display data-storing process (S62) the display device control unit 25 causes the target image temporary storage unit 26 to output the target image data which is temporarily stored in the target image temporary storage unit 26 and causes the image storage unit 27 to store the target image data output from the target image temporary storage unit 26. Accordingly, the target image temporary storage unit 26 outputs the target image data which is temporarily stored in the target image temporary storage unit 26 to the image storage unit 27. The image storage unit 27 stores the target image data output from the target image temporary storage unit 26.

When a still image is displayed on the basis of the display data corresponding to the third still image format and the still image display signal 12 is switched from the ON state to the OFF state, the display data corresponding to the third still image format is temporarily stored in the target image temporary storage unit 26. Accordingly, the display data corresponding to the third still image format is stored by the image storage unit 27.

When the decompressing process is performed on the third still image data corresponding to the third still image format and the still image display signal 12 is switched from the ON state to the OFF state, the display data corresponding to the second still image format is temporarily stored in the target image temporary storage unit 26. Accordingly, the display data corresponding to the second still image format is stored by the image storage unit 27.

When the decompressing process is performed on the second still image data corresponding to the second still image format and the still image display signal 12 is switched from the ON state to the OFF state, there is no display data temporarily stored in the target image temporary storage unit 26. Accordingly, the display data is not stored by the image storage unit 27. Accordingly, in the display data-storing process (S62), the display data corresponding to the second still image data or the third still image data having image quality equal to or higher than the image quality of the first still image data is stored. By the above-mentioned process flow, the management data-receiving process (S50) is performed.

Figure 14:
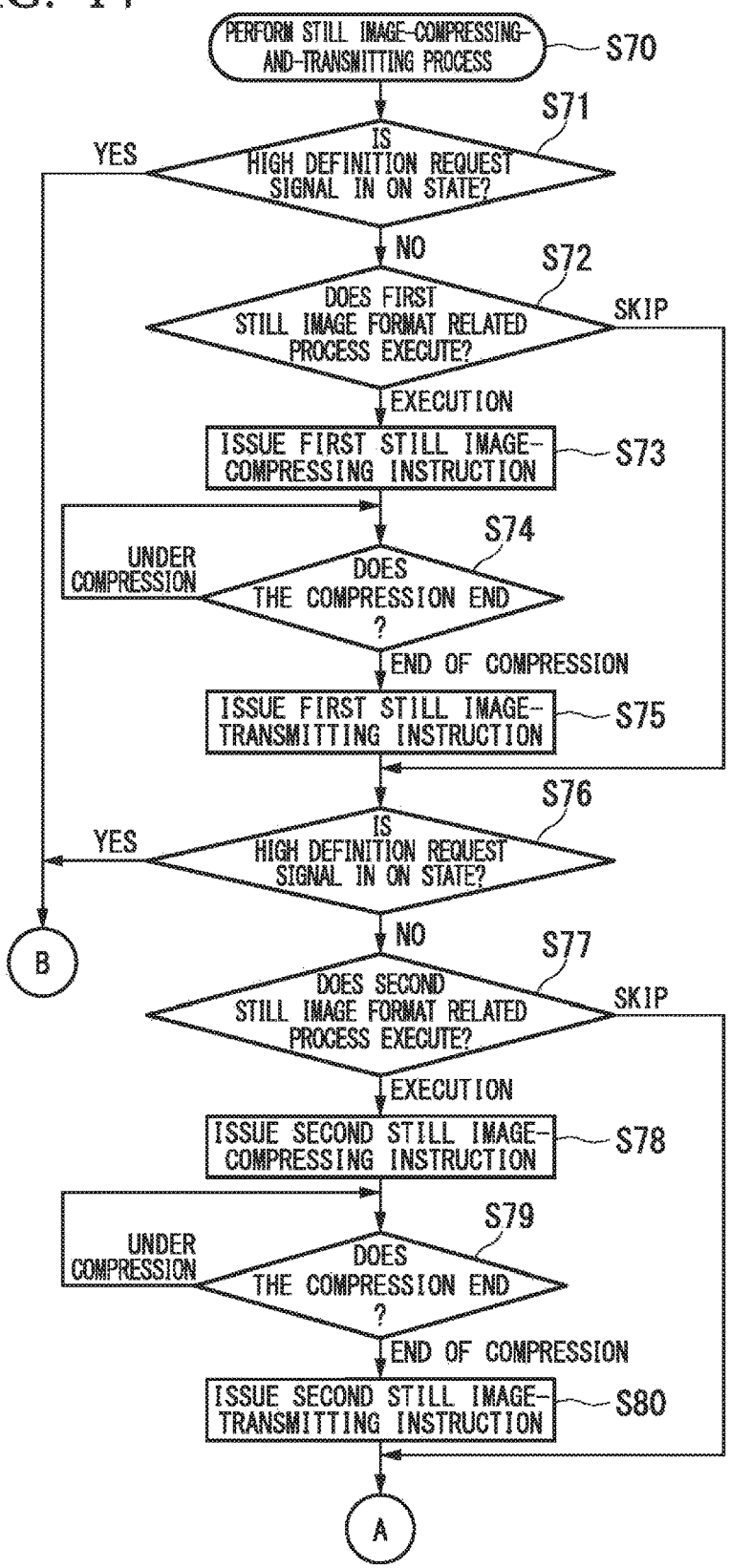
FIG. 14 is a flowchart illustrating an example of an operation of the endoscope according to the second embodiment of the present invention.
Figures 15, 16:
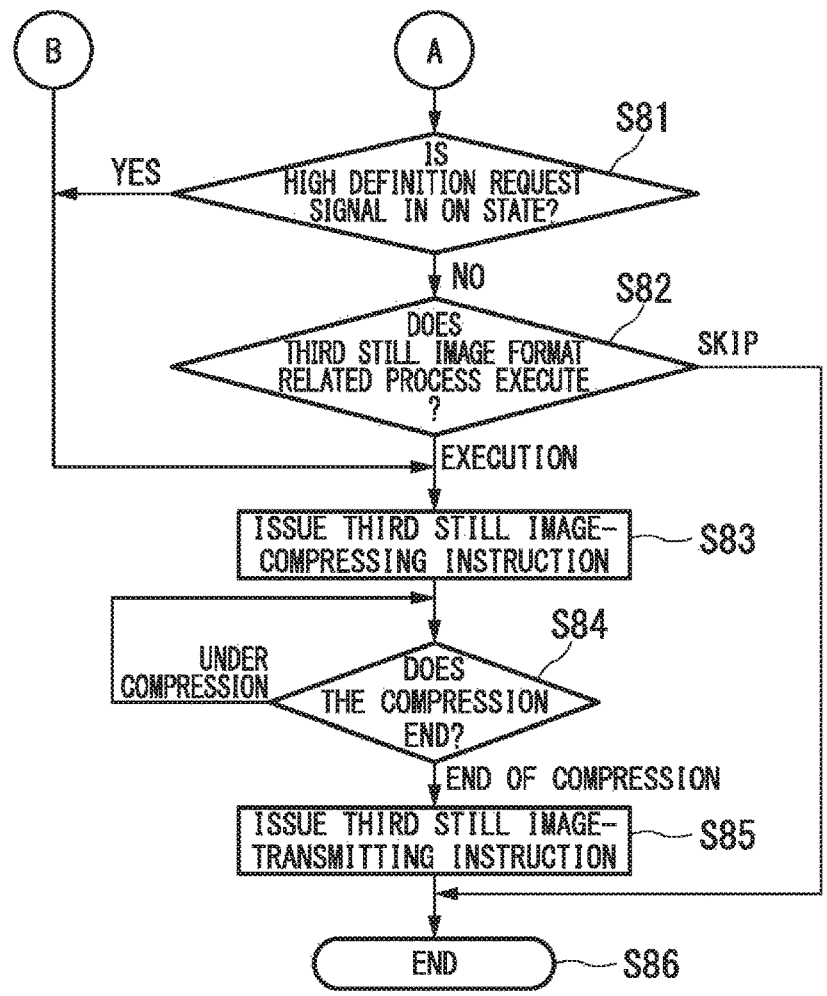
FIG. 15 is a flowchart illustrating an example of the operation of the endoscope according to the second embodiment of the present invention.
FIG. 16 is a reference diagram illustrating an example of details of a selection table in the second embodiment of the present invention.

Details of the processes of the display quality-selecting function and the preferential display function will be described below with reference to FIGS. 14 to 16. FIGS. 14 and 15 illustrate an example of a flow of a still image-compressing-and-transmitting process (S70) which is performed by the endoscope 20. FIG. 16 illustrates an example of details of a selection table which is used for the endoscope 20 to determine whether to perform a process for each still image format.

As illustrated in FIG. 16, the selection table is a table in which information indicating a still image format and information indicating execution or skip (omission) are correlated. The information indicating the still image format indicates any one of the first still image format, the second still image format, and the third still image format. The information indicating execution or skip indicates any one of execution and skip of a process associated with the correlated still image format.

As illustrated in FIG. 16, the information indicating execution is correlated with the information indicating the first still image format and the information indicating the third still image format. Accordingly, control is performed to perform a process associated with the first still image format and a process associated with the third still image format. The information indicating skip is correlated with the information indicating the second still image format. Accordingly, control is performed so as not to perform a process associated with the second still image format. The endoscope control unit 22 serves as a storage unit that stores a selection table (execution information) in advance. The endoscope control unit 22 performs control associated with generation of the still image data on the basis of the stored selection table.

Details of the still image-compressing-and-transmitting process (S70) will be described below with reference to FIGS. 14 and 15. The still image-compressing-and-transmitting process (S70) is a process which is obtained by adding processes associated with the display quality-selecting function and the preferential display function to the still image-compressing-and-transmitting process (S20) in the first embodiment. Processes not associated with the display quality-selecting function and the preferential display function are the same as the still image-compressing-and-transmitting process (S20).

First, the endoscope control unit 22 monitors the high definition request signal 23 from the freeze-instructing unit 21 and determines whether the high definition request signal 23 is in the ON state (S71). When the high definition request signal 23 is in the ON state, a third still image-compressing instruction (S83) is issued. When the high definition request signal 23 is in the OFF state, the endoscope control unit 22 performs a first still image format execution-determining process (S72). In the first still image format execution-determining process (S72), the endoscope control unit 22 determines whether generation of the first still image data of the first still image format should be executed on the basis of the selection table.

When information correlated with the information indicating the first still image format in the selection table indicates skip, the processes of S73 to S75 are not performed but the process of S76 is performed. When information correlated with the information indicating the first still image format in the selection table indicates execution, the endoscope control unit 22 issues a first still image-compressing instruction (S73). Since the first still image-compressing instruction (S73) is the same as the first still image-compressing instruction (S21) in the first embodiment, description of the first still image-compressing instruction (S73) will not be repeated.

Subsequently, the endoscope control unit 22 detects a state of the still image-compressing process which is performed by the still image-compressing unit 6 by a processing state-determining process (S74). The processing state-determining process (S74) is repeatedly performed while the still image-compressing process continues. When end of the still image-compressing process is detected, the endoscope control unit 22 issues a first still image-transmitting instruction (S75). Since the first still image-transmitting instruction (S75) is the same as the first still image-transmitting instruction (S23) in the first embodiment, description of the first still image-transmitting instruction (S75) will not be repeated.

Subsequently, the endoscope control unit 22 monitors the high definition request signal 23 from the freeze-instructing unit 21 and determines whether the high definition request signal 23 is in the ON state (S76). When the high definition request signal 23 is in the ON state, a third still image-compressing instruction (S83) is issued. When the high definition request signal 23 is in the OFF state, the endoscope control unit 22 performs a second still image format execution-determining process (S77). In the second still image format execution-determining process (S77), the endoscope control unit 22 determines whether generation of the second still image data of the second still image format should be executed on the basis of the selection table.

When information correlated with the information indicating the second still image format in the selection table indicates skip, the processes of S78 to S80 are not performed but the process of S81 is performed. When information correlated with the information indicating the second still image format in the selection table indicates execution, the endoscope control unit 22 issues a second still image-compressing instruction (S78). Since the second still image-compressing instruction (S78) is the same as the second still image-compressing instruction (S24) in the first embodiment, description of the second still image-compressing instruction (S78) will not be repeated.

Subsequently, the endoscope control unit 22 detects a state of the still image-compressing process which is performed by the still image-compressing unit 6 by a processing state-determining process (S79). The processing state-determining process (S79) is repeatedly performed while the still image-compressing process continues. When end of the still image-compressing process is detected, the endoscope control unit 22 issues a second still image-transmitting instruction (S80). Since the second still image-transmitting instruction (S80) is the same as the second still image-transmitting instruction (S26) in the first embodiment, description of the second still image-transmitting instruction (S80) will not be repeated.

Subsequently, the endoscope control unit 22 monitors the high definition request signal 23 from the freeze-instructing unit 21 and determines whether the high definition request signal 23 is in the ON state (S81). When the high definition request signal 23 is in the ON state, a third still image-compressing instruction (S83) is issued. When the high definition request signal 23 is in the OFF state, the endoscope control unit 22 performs a third still image format execution-determining process (S82). In the third still image format execution-determining process (S82), the endoscope control unit 22 determines whether generation of the third still image data of the third still image format should be executed on the basis of the selection table.

When information correlated with the information indicating the third still image format in the selection table indicates skip, the processes of S83 to S85 are not performed and the still image-compressing-and-transmitting process (S70) ends (S86). When information correlated with the information indicating the third still image format in the selection table indicates execution, the endoscope control unit 22 issues a third still image-compressing instruction (S83). Since the third still image-compressing instruction (S83) is the same as the third still image-compressing instruction (S27) in the third embodiment, description of the second still image-compressing instruction (S83) will not be repeated.

Subsequently, the endoscope control unit 22 detects a state of the still image-compressing process which is performed by the still image-compressing unit 6 by a processing state-determining process (S84). The processing state-determining process (S84) is repeatedly performed while the still image-compressing process continues. When end of the still image-compressing process is detected, the endoscope control unit 22 issues a third still image-transmitting instruction (S85). Since the third still image-transmitting instruction (S85) is the same as the third still image-transmitting instruction (S29) in the first embodiment, description of the third still image-transmitting instruction (S85) will not be repeated.

When the third still image-transmitting instruction (S85) is issued, the still image-compressing-and-transmitting process (S70) ends (S86). The display quality-selecting function and the preferential display function are realized by the above-mentioned process flow.

Figure 17:
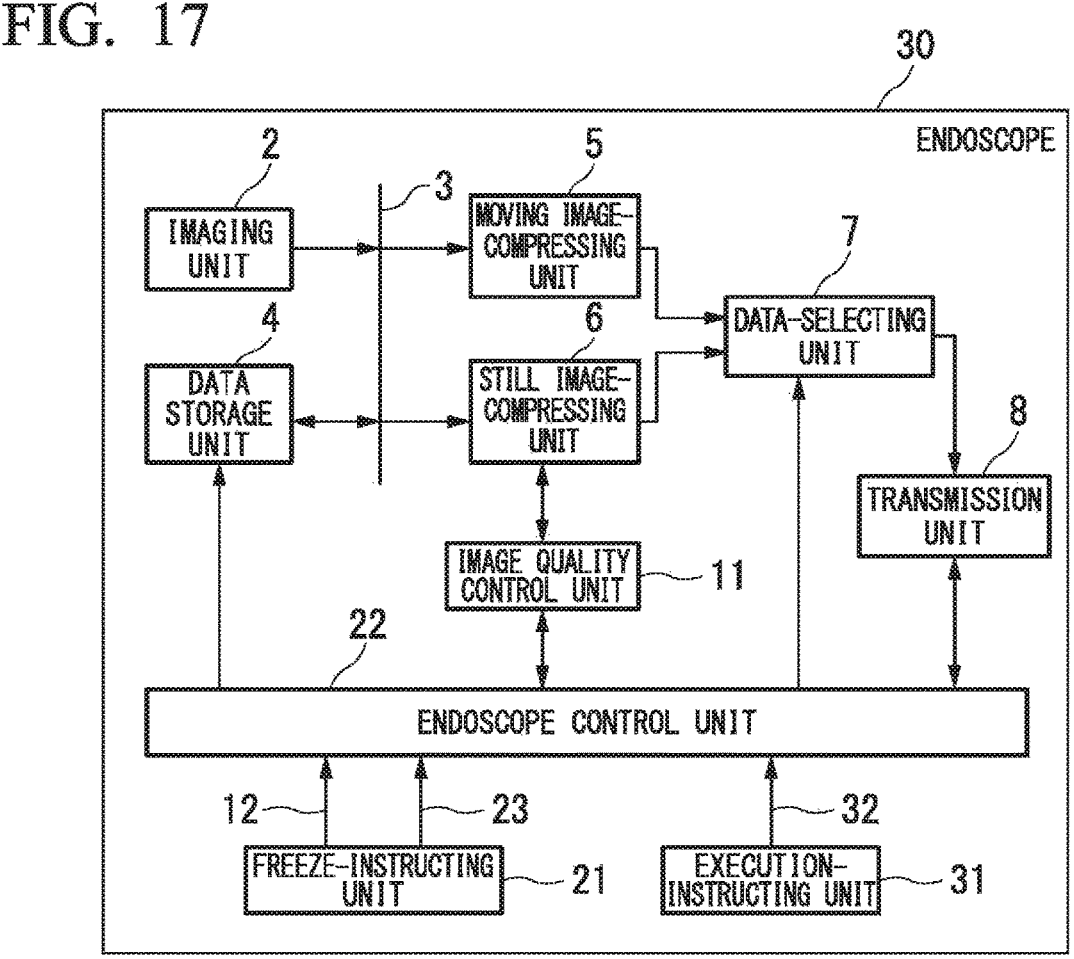
FIG. 17 is a block diagram illustrating a variant of a configuration of the endoscope according to the second embodiment of the present invention.

Details of the selection table illustrated in FIG. 16 may be arbitrarily changed. That is, in the selection table, the information indicating execution or skip may be arbitrarily changed. FIG. 17 illustrates an example of a configuration of an endoscope in which details of the selection table can be changed. As illustrated in FIG. 17, in the endoscope 30, an execution-instructing unit 31 is added to the configuration of the endoscope 20 illustrated in FIG. 11.

An operator of the endoscope 30 inputs information for designating details of the selection table by operating the execution-instructing unit 31. The execution-instructing unit 31 instructs whether to execute display processes of a plurality of pieces of still image data by outputting an execution instruction signal 32 based on the input information to the endoscope control unit 22. The endoscope control unit 22 rewrites details of the selection table stored in the endoscope control unit 22 on the basis of the execution instruction signal 32. Since the other configuration is the same as the configuration of the endoscope 20, description of the other configuration will not be repeated.

In the endoscope 30 illustrated in FIG. 17, it may be arbitrarily set whether to display each of the plurality of pieces of still image data. That is, it can be arbitrarily set whether to display each of the first still image data of the first still image format, the second still image data of the second still image format, and the third still image data of the third still image format. For example, only the second still image data cannot be displayed using the selection table illustrated in FIG. 16. An operator of the endoscope 30 can arbitrarily set which still image data to display or which still image data not to display.

In the wireless endoscope system according to this embodiment, the automatic storage function, the display quality-selecting function, and the preferential display function are installed, but only one or only two of the three functions may be installed.

For example, when the automatic storage function is not installed, the target image temporary storage unit 26 and the image storage unit 27 are not necessary. In the management data-receiving process (S50) illustrated in FIG. 13, the still image format-determining process (S58), the temporary storage-instructing process (S59), the decompressed still image format-determining process (S61), and the display data-storing process (S62) are not necessary.

When the display quality-selecting function is not installed, the first still image format execution-determining process (S72), the second still image format execution-determining process (S77), and the third still image format execution-determining process (S82) in the still image-compressing-and-transmitting process (S70) illustrated in FIGS. 14 and 15 are not necessary. In addition, the selection table illustrated in FIG. 16 is not necessary.

When the preferential display function is not installed, the high definition request signal 23 is not necessary. Accordingly, the freeze-instructing unit 21 may be the freeze-instructing unit 9 in the first embodiment. In the still image-compressing-and-transmitting process (S70) illustrated in FIGS. 14 and 15, the high definition request signal-determining processes (S71, S76, and S81) are not necessary.

In this embodiment, details of the processes illustrated in FIGS. 13 to 15 can be appropriately changed.

In this embodiment, image quality of a plurality of pieces of still image data is controlled such that the image quality of the still image data generated later becomes higher. Accordingly, it is possible to decrease an initial display delay of a still image, to decrease a size of the endoscope 20, and to reduce power consumption of the endoscope 20.

By installing the automatic storage function, it is possible to reduce labor of an operator of the endoscope 20 which is required for storing display data for displaying a target image.

By installing the display quality-selecting function, it is possible to display a still image with image quality which is desired by the operator of the endoscope 20.

By installing the preferential display function, it is possible to display a still image with highest image quality immediately when the operator of the endoscope 20 requests display of the still image with highest image quality. Since the still image with the highest image quality is displayed immediately after the request is issued from the operator of the endoscope 20, it is possible to improve operability associated with detailed diagnosis of an affected part or the like.

While embodiments of the present invention have been described with reference to the accompanying drawings, the detailed configuration of the present invention is not limited to the above-mentioned embodiments and also includes modifications in design without departing from the gist of the present invention. The present invention is not limited to the above description but is defined only by the appended claims.

What is claimed is:

1. A wireless endoscope system, comprising:
    an imaging unit that captures an image and generates imaging data;
    a freeze-instructing unit that generates a still image display signal relevant to an execution of a still image display;
    a data storage unit that stores the imaging data as storage data at a time at which the still image display signal is switched from a first state indicating an execution of a moving image display to a second state indicating the execution of the still image display;
    a moving image-compressing unit that performs a moving image-compressing process on the imaging data and generates moving image data;
    a still image-compressing unit that performs a still image-compressing process on the storage data and generates a plurality of pieces of still image data;
    an image quality control unit that controls image quality of the plurality of pieces of still image data such that image quality of a piece of still image data generated later among the plurality of pieces of still image data becomes higher;
    a data-selecting unit that selects the moving image data when the still image display signal is in the first state, and sequentially selects the plurality of pieces of still image data in an order in which the plurality of pieces of still image data are generated when the still image display signal is in the second state;
    a transmission unit that transmits the moving image data or the plurality of pieces of still image data selected by the data-selecting unit in a wireless manner;
    a reception unit that receives the moving image data or the plurality of pieces of still image data transmitted from the transmission unit in a wireless manner;
    an image-decompressing unit that performs a decompressing process on the moving image data or the plurality of pieces of still image data received by the reception unit and generates display data, the image-decompressing unit generating a plurality of pieces of the display data in an order in which the plurality of pieces of still image data are generated in the decompressing process on the plurality of pieces of still image data;
    an image display unit that performs a display process based on the display data;
    a target image-designating unit that designates the display data as target image data when the image quality of the piece of still image data is equal to or higher than a predetermined image quality;
    an image storage unit that stores the display data designated as the target image data; and
    a high image quality requesting unit that generates a high definition request signal relevant to a request for a piece of still image data with a predetermined highest image quality,
    wherein the image quality control unit sets the image quality of the piece of still image data to the highest image quality when the still image display signal is in the second state and the high definition request signal is in a third state indicating a request for still image data with the highest image quality before a final piece of still image data among the plurality of pieces of still image data is generated, and
    the image quality control unit gradually changes the image quality of the plurality of pieces of still image data such that the image quality of the piece of still image data generated later becomes higher and image quality of a piece of still image data generated finally becomes the highest image quality when the still image display signal is in the second state and the high definition request signal is in a fourth state other than the third state before the final piece of still image data among the plurality of pieces of still image data is generated.

2. The wireless endoscope system according to claim 1, wherein the target image-designating unit that designates the display data as target image data when image quality of a piece of still image data corresponding to the display data generated by the image-decompressing unit at a time immediately before the still image display signal is switched from the second state to the first state is equal to or higher than a predetermined image quality.

3. The wireless endoscope system according to claim 1, further comprising an endoscope control unit that controls a generation of the plurality of pieces of still image data on the basis of execution information indicating whether generation of each of the plurality of pieces of still image data should be executed.

4. An endoscope, comprising:
    an imaging unit that captures an image and generates imaging data;
    a freeze-instructing unit that generates a still image display signal relevant to an execution of a still image display;

a data storage unit that stores the imaging data as storage data at a time at which the still image display signal is switched from a first state indicating an execution of a moving image display to a second state indicating an execution of the still image display;
a moving image-compressing unit that performs a moving image-compressing process on the imaging data and generates moving image data;
a still image-compressing unit that performs a still image-compressing process on the storage data and generates a plurality of pieces of still image data;
an image quality control unit that controls image quality of the plurality of pieces of still image data such that image quality of a piece of still image data generated later among the plurality of pieces of still image data becomes higher;
a data-selecting unit that selects the moving image data when the still image display signal is in the first state and sequentially selects the plurality of pieces of still image data in an order in which the plurality of pieces of still image data are generated when the still image display signal is in the second state;
a transmission unit that transmits the moving image data or the plurality of pieces of still image data selected by the data-selecting unit in a wireless manner; and
a high image quality-requesting unit that generates a high definition request signal relevant to a request for a piece of still image data with a predetermined highest image quality,
wherein the image quality control unit sets the image quality of the piece of still image data to the highest image quality when the still image display signal is in the second state and the high definition request signal is in a third state indicating a request for still image data with the highest image quality before a final piece of still image data among the plurality of pieces of still image data is generated, and
the image quality control unit gradually changes the image quality of the plurality of pieces of still image data such that the image quality of the piece of still image data generated later becomes higher and image quality of a piece of still image data generated finally becomes the highest image quality when the still image display signal is in the second state and the high definition request signal is in a fourth state other than the third state before the final piece of still image data among the plurality of pieces of still image data is generated.

5. A display device, comprising:
a reception unit that receives moving image data or a plurality of pieces of still image data transmitted from an endoscope in a wireless manner;
an image-decompressing unit that performs a decompressing process on the moving image data or the plurality of pieces of still image data received by the reception unit and generates display data, the image-decompressing unit generating a plurality of pieces of the display data in an order in which the plurality of pieces of still image data are generated in the decompressing process on the plurality of pieces of still image data; and
an image display unit that performs a display process based on the display data,
wherein the endoscope includes;
an imaging unit that captures an image and generates imaging data,
a freeze-instructing unit that generates a still image display signal relevant to an execution of a still image display,
a data storage unit that stores the imaging data as storage data at a time at which the still image display signal is switched from a first state indicating an execution of a moving image display to a second state indicating an execution of the still image display,
a moving image-compressing unit that performs a moving image-compressing process on the imaging data and generates the moving image data,
a still image-compressing unit that performs a still image-compressing process on the storage data and generates the plurality of pieces of still image data,
an image quality control unit that controls image quality of the plurality of pieces of still image data such that image quality of a piece of still image data generated later among the plurality of pieces of still image data becomes higher,
a data-selecting unit that selects the moving image data when the still image display signal is in the first state and sequentially selects the plurality of pieces of still image data in the order in which the plurality of pieces of still image data are generated when the still image display signal is in the second state,
a transmission unit that transmits the moving image data or the plurality of pieces of still image data selected by the data-selecting unit in a wireless manner; and
a high image quality requesting unit that generates a high definition request signal relevant to a request for a piece of still image data with a predetermined highest image quality,
wherein the image quality control unit sets the image quality of the piece of still image data to the highest image quality when the still image display signal is in the second state and the high definition request signal is in a third state indicating a request for still image data with the highest image quality before a final piece of still image data among the plurality of pieces of still image data is generated, and
the image quality control unit gradually changes the image quality of the plurality of pieces of still image data such that the image quality of the piece of still image data generated later becomes higher and image quality of a piece of still image data generated finally becomes the highest image quality when the still image display signal is in the second state and the high definition request signal is in a fourth state other than the third state before the final piece of still image data among the plurality of pieces of still image data is generated.

6. An image transmission method, comprising:
a step of generating a still image display signal relevant to an execution of a still image display by a freeze-instructing unit;
a step of storing imaging data which is generated by an imaging unit capturing an image as storage data at a time at which the still image display signal is switched from a first state indicating an execution of a moving image display to a second state indicating an execution of the still image display;
a step of performing a moving image-compressing process on the imaging data to generate moving image data by a moving image-compressing unit;

a step of performing a still image-compressing process on the storage data by a still image-compressing unit to generate a plurality of pieces of still image data such that image quality of a piece of still image data generated later among the plurality of pieces of still image data becomes higher;

a step of transmitting the moving image data in a wireless manner by a transmission unit when the still image display signal is in the first state;

a step of transmitting the plurality of pieces of still image data in a wireless manner in an order in which the plurality of pieces of still image data are generated by the transmission unit when the still image display signal is in the second state; and a step of setting the image quality of the piece of still image data to the highest image quality when the still image display signal is in the second state and the high definition request signal is in a third state indicating a request for still image data with the highest image quality before a final piece of still image data among the plurality of pieces of still image data is generated; and a step of gradually changes the image quality of the plurality of pieces of still image data such that the image quality of the piece of still image data generated later becomes higher and image quality of a piece of still image data generated finally becomes the highest image quality when the still image display signal is in the second state and the high definition request signal is in a fourth state other than the third state before the final piece of still image data among the plurality of pieces of still image data is generated.

7. An image display method, comprising:

a step of receiving moving image data or a plurality of pieces of still image data transmitted from an endoscope in a wireless manner by a reception unit;

a step of performing a decompressing process on the moving image data or the plurality of pieces of still image data received by the reception unit to generate display data, and generating a plurality of pieces of display data in an order in which the plurality of pieces of still image data are generated in the decompressing process on the plurality of pieces of still image data by an image-decompressing unit; and a step of performing a display process based on the display data by an image display, wherein the endoscope includes an imaging unit that captures an image and generates imaging data, a freeze-instructing unit that generates a still image display signal relevant to an execution of a still image display, a data storage unit that stores the imaging data as storage data at a time at which the still image display signal is switched from a first state indicating an execution of a moving image display to a second state indicating an execution of the still image display, a moving image-compressing unit that performs a moving image-compressing process on the imaging data and generates the moving image data, a still image-compressing unit that performs a still image-compressing process on the storage data and generates the plurality of pieces of still image data, an image quality control unit that controls image quality of the plurality of pieces of still image data such that image quality of a piece of still image data generated later among the plurality of pieces of still image data becomes higher, a data-selecting unit that selects the moving image data when the still image display signal is in the first state and sequentially selects the plurality of pieces of still image data in the order in which the plurality of pieces of still image data are generated when the still image display signal is in the second state, a transmission unit that transmits the moving image data or the plurality of pieces of still image data selected by the data-selecting unit in a wireless manner, and a high image quality-requesting unit that generates a high definition request signal relevant to a request for a piece of still image data with a predetermined highest image quality, wherein the image quality control unit sets the image quality of the piece of still image data to the highest image quality when the still image display signal is in the second state and the high definition request signal is in a third state indicating a request for still image data with the highest image quality before a final piece of still image data among the plurality of pieces of still image data is generated, and the image quality control unit gradually changes the image quality of the plurality of pieces of still image data such that the image quality of the piece of still image data generated later becomes higher and image quality of a piece of still image data generated finally becomes the highest image quality when the still image display signal is in the second state and the high definition request signal is in a fourth state other than the third state before the final piece of still image data among the plurality of pieces of still image data is generated.

8. A non-transitory computer-readable computer medium storing a program causing a computer to perform:

a step of detecting a still image display signal relevant to an execution of a still image display which is generated by a freeze-instructing unit;

a step of causing a data storage unit to store imaging data which is generated by an imaging unit capturing an image as storage data at a time at which the still image display signal is switched from a first state indicating an execution of a moving image display to a second state indicating an execution of the still image display;

a step of causing a moving image-compressing unit to perform a process of performing a moving image-compressing process on the imaging data and generating moving image data;

a step of causing a still image-compressing unit to perform a process of performing a still image-compressing process on the storage data and generating a plurality of pieces of still image data such that image quality of a piece of still image data generated later among the plurality of pieces of still image data becomes higher;

a step of causing a transmission unit to transmit the moving image data in a wireless manner when the still image display signal is in the first state;

a step of causing the transmission unit to transmit the plurality of pieces of still image data in a wireless manner in an order in which the plurality of pieces of still image data are generated when the still image display signal is in the second state;

a step of setting the image quality of the piece of still image data to the highest image quality when the still image display signal is in the second state and the high definition request signal is in a third state indicating a request for still image data with the highest image quality before a final piece of still image data among the plurality of pieces of still image data is generated; and a step of gradually changes the image quality of the plurality of pieces of still image data such that the image quality of the piece of still image data generated later becomes higher and image quality of a piece of still image data generated finally becomes the highest image quality when the still image display signal is in the second state and the high definition request signal is in a fourth state other than the third state before the final piece of still image data among the plurality of pieces of still image data is generated.

9. A non-transitory computer-readable computer medium storing a program causing a computer to perform:

a step of causing a reception unit to receive moving image data or a plurality of pieces of still image data transmitted from an endoscope in a wireless manner;

a step of causing an image-decompressing unit to perform a decompressing process on the moving image data or the plurality of pieces of still image data received by the reception unit to generate display data, and causing the image-decompressing unit to generate a plurality of pieces of display data in an order in which the plurality of pieces of still image data are generated in the decompressing process on the plurality of pieces of still image data; and a step of causing an image display unit to perform a display process based on the display data, wherein the endoscope includes
an imaging unit that captures an image and generates imaging data,
a freeze-instructing unit that generates a still image display signal relevant to an execution of a still image display,
a data storage unit that stores the imaging data as storage data at a time at which the still image display signal is switched from a first state indicating an execution of a moving image display to a second state indicating an execution of the still image display,
a moving image-compressing unit that performs a moving image-compressing process on the imaging data and generates the moving image data,
a still image-compressing unit that performs a still image-compressing process on the storage data and generates the plurality of pieces of still image data,
an image quality control unit that controls image quality of the plurality of pieces of still image data such that image quality of a piece of still image data generated later among the plurality of pieces of still image data becomes higher,
a data-selecting unit that selects the moving image data when the still image display signal is in the first state and sequentially selects the plurality of pieces of still image data in the order in which the plurality of pieces of still image data are generated when the still image display signal is in the second state,
a transmission unit that transmits the moving image data or the plurality of pieces of still image data selected by the data-selecting unit in a wireless manner,
a high image quality-requesting unit that generates a high definition request signal relevant to a request for a piece of still image data with a predetermined highest image quality,
wherein the image quality control unit sets the image quality of the piece of still image data to the highest image quality when the still image display signal is in the second state and the high definition request signal is in a third state indicating a request for still image data with the highest image quality before a final piece of still image data among the plurality of pieces of still image data is generated, and
the image quality control unit gradually changes the image quality of the plurality of pieces of still image data such that the image quality of the piece of still image data generated later becomes higher and image quality of a piece of still image data generated finally becomes the highest image quality when the still image display signal is in the second state and the high definition request signal is in a fourth state other than the third state before the final piece of still image data among the plurality of pieces of still image data is generated.

* * * * *